United States Patent
Yamano et al.

(10) Patent No.: US 11,311,524 B2
(45) Date of Patent: Apr. 26, 2022

(54) PHARMACEUTICAL COMPOSITION USED FOR TREATMENT OF HTLV-1-ASSOCIATED MYELOPATHY

(71) Applicants: DAIICHI SANKYO COMPANY, LIMITED, Tokyo (JP); ST. MARIANNA UNIVERSITY SCHOOL OF MEDICINE, Kawasaki (JP)

(72) Inventors: Yoshihisa Yamano, Kanagawa (JP); Natsumi Ueda, Kanagawa (JP); Kazushi Araki, Tokyo (JP)

(73) Assignees: DAIICHI SANKYO COMPANY, LIMITED, Tokyo (JP); ST. MARIANNA UNIVERSITY SCHOOL OF MEDICINE, Kawasaki (JP)

( * ) Notice: Subject to any disclaimer, the term of this patent is extended or adjusted under 35 U.S.C. 154(b) by 342 days.

(21) Appl. No.: 16/477,286

(22) PCT Filed: Jan. 18, 2018

(86) PCT No.: PCT/JP2018/001301
§ 371 (c)(1),
(2) Date: Jul. 11, 2019

(87) PCT Pub. No.: WO2018/135556
PCT Pub. Date: Jul. 26, 2018

(65) Prior Publication Data
US 2019/0343816 A1    Nov. 14, 2019

(30) Foreign Application Priority Data
Jan. 19, 2017 (JP) .............................. JP2017-007887

(51) Int. Cl.
| A61K 31/5375 | (2006.01) |
| A61K 31/4427 | (2006.01) |
| A61K 31/443 | (2006.01) |
| A61P 25/00 | (2006.01) |

(52) U.S. Cl.
CPC ............ *A61K 31/443* (2013.01); *A61P 25/00* (2018.01)

(58) Field of Classification Search
CPC ...................... A61K 31/5375; A61K 31/4427
USPC ..................... 514/231.5, 338, 339
See application file for complete search history.

(56) References Cited

U.S. PATENT DOCUMENTS

| 2012/0264734 A1 | 10/2012 | Kuntz et al. |
| 2013/0053397 A1 | 2/2013 | Brackley et al. |
| 2017/0073335 A1 | 3/2017 | Kanno et al. |
| 2018/0200238 A1 | 7/2018 | Watanabe et al. |

FOREIGN PATENT DOCUMENTS

| CN | 102970869 A | 3/2013 |
| CN | 104080769 A | 10/2014 |
| CN | 106132954 A | 11/2016 |
| JP | 6009135 B1 | 10/2016 |
| WO | WO-2011/129424 A1 | 10/2011 |
| WO | WO-2011/140324 A1 | 11/2011 |
| WO | WO-2012/142504 A1 | 10/2012 |
| WO | WO-2015/141616 A1 | 9/2015 |
| WO | WO-2016/073956 A1 | 5/2016 |

OTHER PUBLICATIONS

International Searching Authority, "International Search Report," issued in connection with International Patent Application No. PCT/JP2018/001301, dated Mar. 20, 2018.
International Searching Authority, "Written Opinion," issued in connection with International Patent Application No. PCT/JP2018/001301, dated Mar. 20, 2018.
Matsuzaki et al., "Advanced in Diagnosis and Treatment of HAM," Journal of Medical Technology, vol. 49, No. 4, Apr. 2005, pp. 409-414.
Yamano, Yoshihisa, "HLTV-1 -Associated Myelopathy (HAM): New development of therapeutic drug based on elucidation of the molecular pathology," Journal of Clinical and Experimental Medicine, vol. 255, No. 5, Oct. 31, 2015, pp. 485-490.
Yang et al., "Structure-Activity Relationship Studies for Enhancer of Zeste Homologue 2 (EZH2) and Enhancer of Zeste Homologue 1 (EZH1) Inhibitors," Journal of Medicinal Chemistry, vol. 59, No. 16, 2016, pp. 7617-7633.
Stazi et al., "EZH2 inhibitors: a patent review (2014-2016)," Expert Opinion on Therapeutic Patents, vol. 27, No. 7, 2017, pp. 797-813.
Araya et al., "Human T-Lymphotropic Virus Type 1 (HTLV-1) and Regulatory T Cells in HTLV-1-Associated Neuroinflammatory Disease," Viruses, vol. 3, 2011, pp. 1532-1548.
Extended European Search Report dated Oct. 20, 2020 for corresponding European Patent Application No. 18741561.7.
Unsong Oh et al: "Treatment of HTLV-I-Associated Myelopathy/Tropical Spastic Paraparesis: Toward Rational Targeted Therapy", Neurologic Clinics, vol. 26, No. 3, Aug. 1, 2008 (Aug. 1, 2008), pp. 781-797.
Office Action dated Jan. 29, 2021 for corresponding Chinese Patent Application No. 201880007277.3.
Office Action dated Dec. 14, 2021 issued in a corresponding Japanese Patent Application No. 2018-562415, (4 pages).

*Primary Examiner* — Raymond J Henley, III
(74) *Attorney, Agent, or Firm* — Foley & Lardner LLP

(57) ABSTRACT

The present invention provides a pharmaceutical composition containing an inhibitor selected from the group consisting of an EZH1 inhibitor, an EZH2 inhibitor and an EZH1/2 dual inhibitor as an active ingredient, for use in treating HTLV-1-associated myelopathy. The present invention provides a pharmaceutical composition for use in treating HTLV-1-associated myelopathy, containing a 1,3-benzodioxole derivative or a pharmaceutically acceptable salt thereof.

11 Claims, 8 Drawing Sheets
Specification includes a Sequence Listing.

FIG. 2
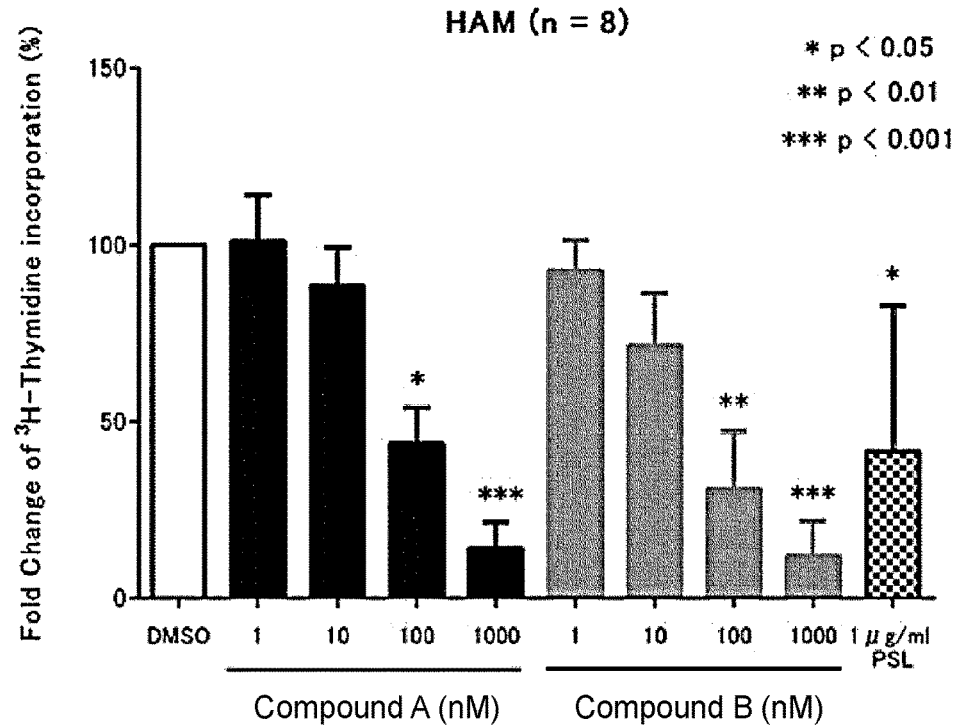
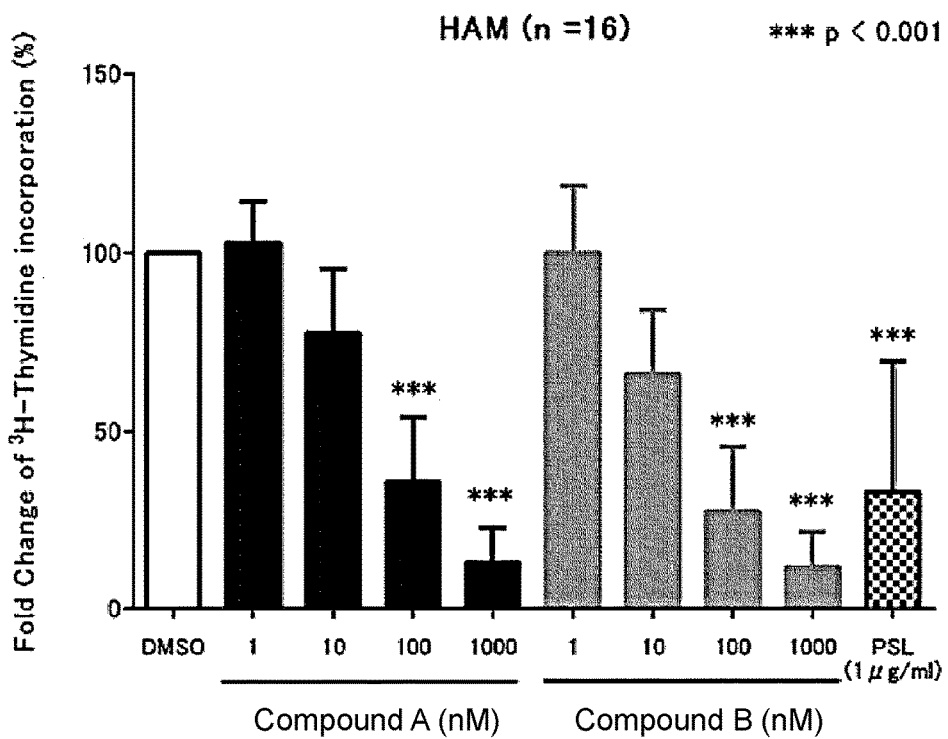

FIG. 3
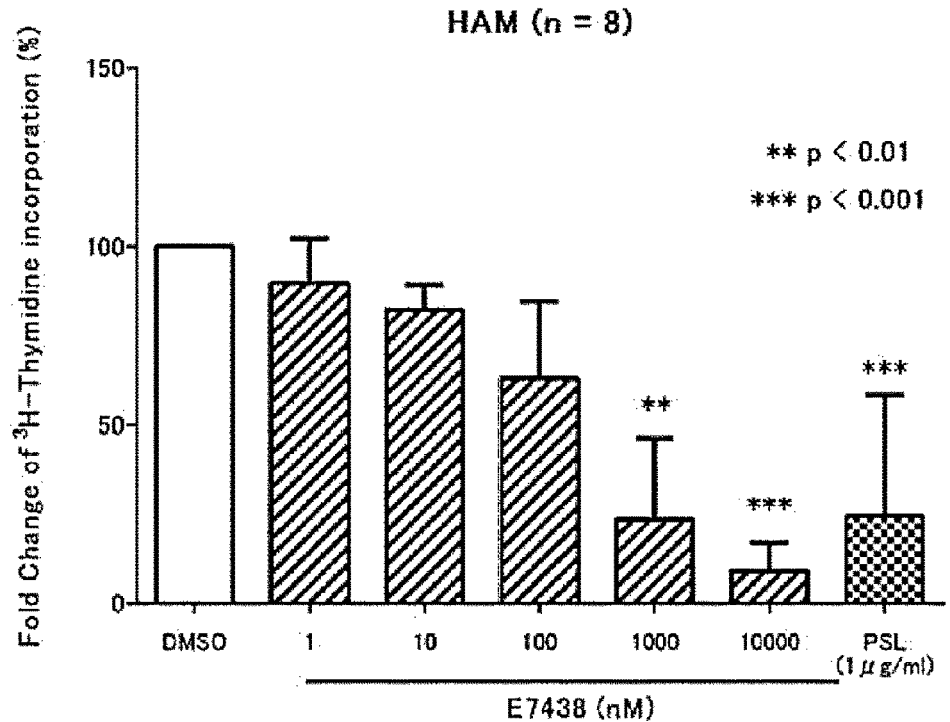
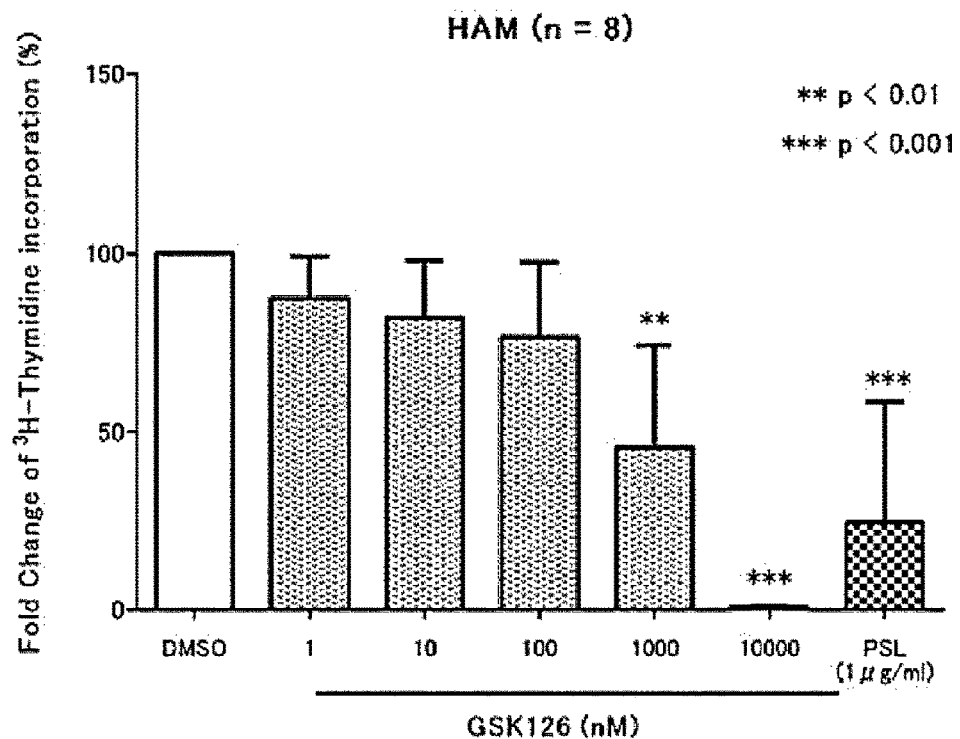

FIG. 6
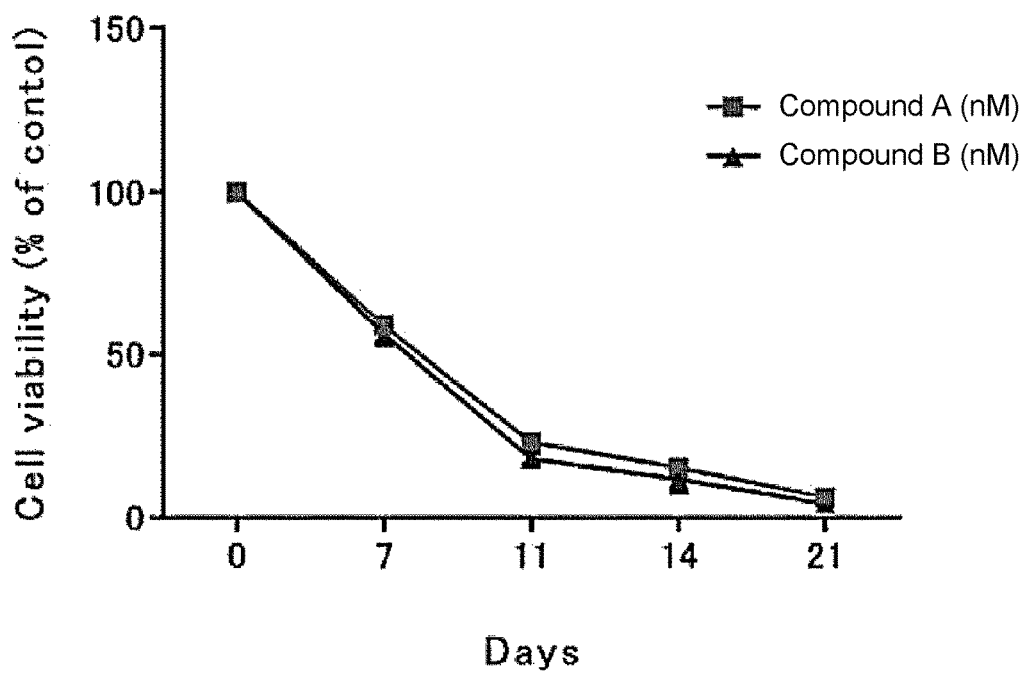
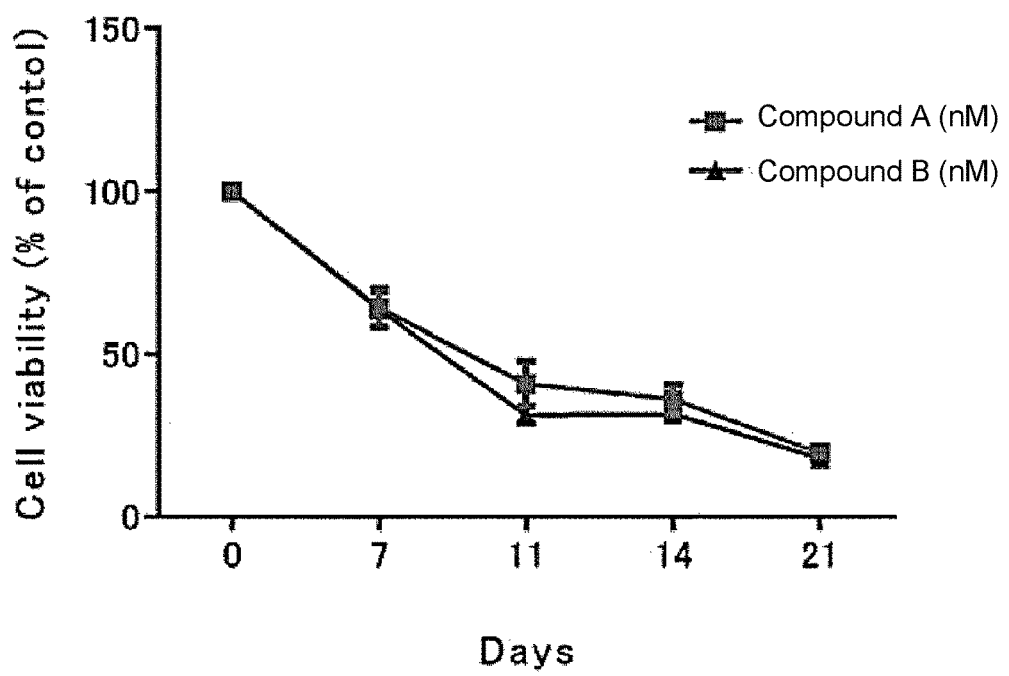

FIG. 7
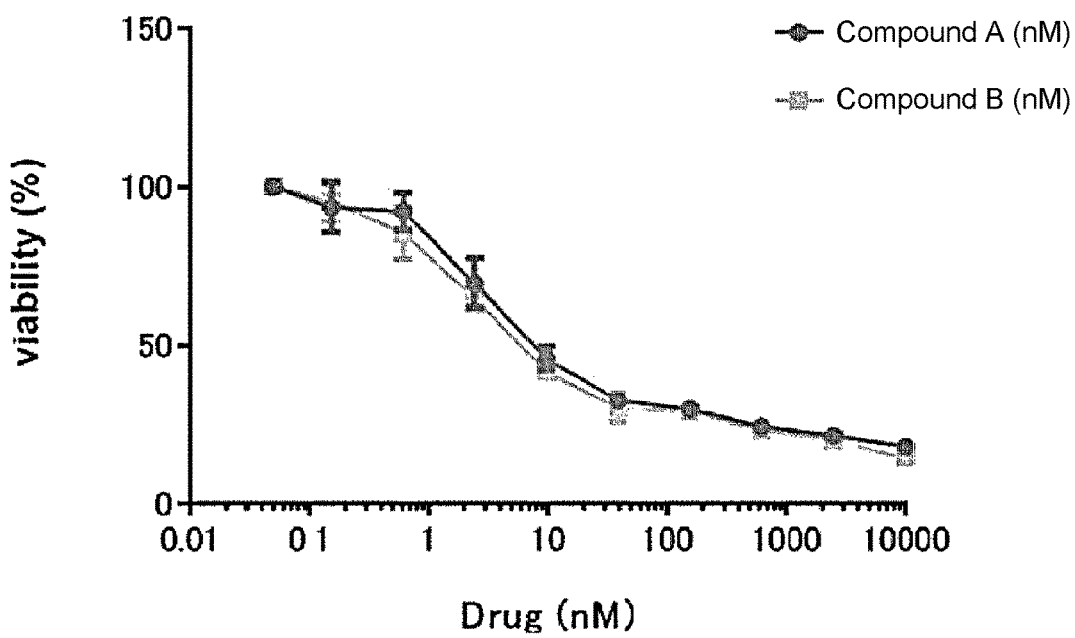
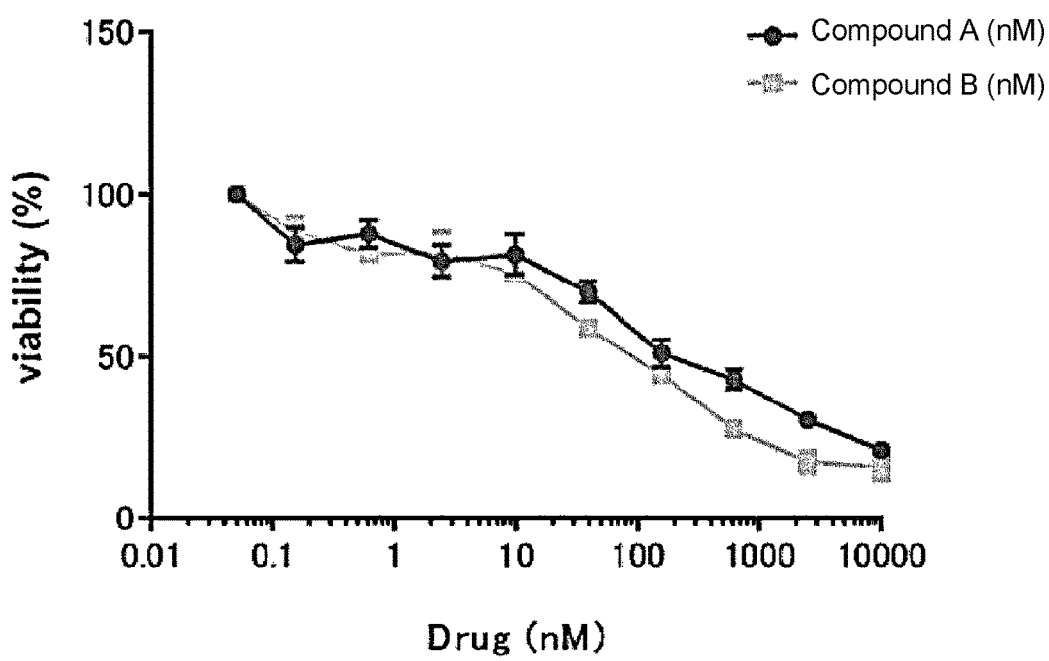

SEQUENCE LISTING

```
<160> NUMBER OF SEQ ID NOS: 2

<210> SEQ ID NO 1
<211> LENGTH: 21
<212> TYPE: DNA
<213> ORGANISM: Artificial Sequence
<220> FEATURE:
<223> OTHER INFORMATION: EZH2#35-F

<400> SEQUENCE: 1
tgtggatact cctccaagga a                                          21

<210> SEQ ID NO 2
<211> LENGTH: 19
<212> TYPE: DNA
<213> ORGANISM: Artificial Sequence
<220> FEATURE:
<223> OTHER INFORMATION: EZH2#35-R

<400> SEQUENCE: 2
gaggagccgt ccttttca                                              19
```

PHARMACEUTICAL COMPOSITION USED FOR TREATMENT OF HTLV-1-ASSOCIATED MYELOPATHY

RELATED APPLICATIONS

The present application claims priority under 37 U.S.C. § 371 to International Patent Application No. PCT/JP2018/001301, filed Jan. 18, 2018, which claims priority to and the benefit of Japanese Patent Application No. 2017-007887, filed on Jan. 19, 2017. The contents of these applications are hereby incorporated by reference in their entireties.

SEQUENCE LISTING

The instant application contains a Sequence Listing which has been submitted in ASCII format via EFS-Web and is hereby incorporated by reference in its entirety. Said ASCII copy, is named 111119-0129_SL.txt and is 1 kb in size.

TECHNICAL FIELD

The present invention relates to a pharmaceutical composition for use in treating HTLV-1-associated myelopathy.

BACKGROUND ART

HTLV-1-associated myelopathy (HAM), which is developed in about 0.25% of the patients infected with human T lymphotropic virus type 1 (HTLV-1), is an intractable neurological disease having no established therapy. The pathological condition of HAM is considered as a nervous tissue disorder caused by excessive immune response due to HTLV-1 infected cells. Steroid and IFNα, which have been used for treatment up to present, have a limited therapeutic effect and less effect on reduction of infected cells, which are considered as a fundamental cause for the disease. In addition to such serious problem, the expression level of HTLV-1 gene is low, unlike the AIDS virus gene, with the result that therapeutic effects by a reverse transcriptase inhibitor and a protease inhibitor were low.

The number of patients who were afflicted with inflammatory diseases associated with HTLV-1 is extremely low. For the reason, elucidation of etiology and development of therapeutic drugs for the diseases have been rarely studied. Incidentally, it has been found that a compound specified in Patent Literature 1 is useful for treating, a kind of tumor, adult T-cell leukemia lymphoma (ATL) (Patent Literature 2). However, adult T-cell leukemia lymphoma (ATL) and HTLV-1-associated myelopathy (HAM) are completely opposite in onset mechanism; more specifically, ATL is a disease developed under immunosuppressive condition; whereas HAM is a disease producing inflammation by immunoenhancement. Accordingly, the therapies and therapeutic agents for them completely differ; more specifically, adult T-cell leukemia lymphoma (ATL) is treated by an anti-cancer agent; whereas, HTLV-1-associated myelopathy (HAM) is treated by an anti-inflammatory agent. Besides, the types of cells involved in pathological conditions of ATL and HAM are completely different, as is apparent from the document (Non Patent Literature 1).

CITATION LIST

Patent Literatures

Patent Literature 1: International Publication No. WO 2015/141616
Patent Literature 2: Japanese Patent No. 6009135

Non Patent Literature

Non Patent Literature 1: Araya N., et al., Viruses, 3: 1532-1548, 2010

SUMMARY OF INVENTION

The present invention provides a pharmaceutical composition for use in treating HTLV-1-associated myelopathy.

The present inventors revealed that a $CD4^+CD25^+CCR4^+$ cell and other $CD4^+$ cells of a patient with HTLV-1-associated myelopathy (HAM) overexpress EZH2. The present inventors found that when autoproliferation activity of PBMC derived from the spinal cord of a patient with HAM is inhibited by an EZH2 inhibitor, IL-10 production ability is enhanced and the number of HTLV-1 infected cells reduces, with the result that apoptosis is induced. The present inventors also found that the effect of the EZH2 inhibitor is further enhanced in a EZH1/2 dual inhibitor. From this, the present inventors were aware that suppressing each of the enzyme activities of EZH1 and EZH2 has a therapeutic significance for HAM. The present invention was attained based on these findings.

More specifically, according to the present invention, the following inventions are provided.

(1) A pharmaceutical composition comprising an inhibitor selected from the group consisting of an EZH1 inhibitor, an EZH2 inhibitor and an EZH1/2 dual inhibitor as an active ingredient, for use in treating HTLV-1-associated myelopathy.

(2) The pharmaceutical composition according to (1), wherein the inhibitor is an EZH1/2 dual inhibitor.

(3) The pharmaceutical composition according to (1), wherein the inhibitor is a compound selected from
N-[(1,2-dihydro-4,6-dimethyl-2-oxo-3-pyridinyl)methyl]-3-methyl-1-[(1S)-1-methylpropyl]-6-[6-(1-piperazinyl)-3-pyridinyl]-1H-indole-4-carboxamide,
N-((4,6-dimethyl-2-oxo-1,2-dihydropyridin-3-yl)methyl)-5-(ethyl(tetrahydro-2H-piran-4-yl)amino)-4-methyl-4'-(morpholinomethyl)-[1,1'-biphenyl]-3-carboxamide,
(2R)-7-bromo-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide, and
(2R)-7-chloro-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide, or a pharmaceutically acceptable salt thereof.

(4) The pharmaceutical composition according to (1) or (2), wherein the inhibitor is (2R)-7-bromo-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide, or (2R)-7-chloro-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide, or a pharmaceutically acceptable salt thereof.

(5) The pharmaceutical composition according to (1) or (2), wherein the inhibitor is (2R)-7-bromo-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide, or a pharmaceutically acceptable salt thereof.

(6) The pharmaceutical composition according to (1) or (2), wherein the inhibitor is (2R)-7-chloro-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide, or a pharmaceutically acceptable salt thereof.

(7) The pharmaceutical composition according to (1) or (2), wherein the inhibitor is (2R)-7-chloro-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide p-toluene sulfonate.

(8) A pharmaceutical composition for use in treating HTLV-1-associated myelopathy, comprising a compound selected from N-[(1,2-dihydro-4,6-dimethyl-2-oxo-3-pyridinyl)methyl]-3-methyl-1-[(1S)-1-methylpropyl]-6-[6-(1-piperazinyl)-3-pyridinyl]-1H-indole-4-carboxamide, N-((4,6-dimethyl-2-oxo-1,2-dihydropyridin-3-yl)methyl)-5-(ethyl(tetrahydro-2H-piran-4-yl)amino)-4-methyl-4'-(morpholinomethyl)-[1,1'-biphenyl]-3-carboxamide, (2R)-7-bromo-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide and (2R)-7-chloro-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide, or a pharmaceutically acceptable salt thereof.

(9) The pharmaceutical composition according to (8), comprising (2R)-7-bromo-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide, or a pharmaceutically acceptable salt thereof.

(10) The pharmaceutical composition according to (8), comprising (2R)-7-chloro-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide, or a pharmaceutically acceptable salt thereof.

(11) The pharmaceutical composition according to (8), comprising (2R)-7-chloro-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide p-toluene sulfonate.

(12) A method for treating HTLV-1-associated myelopathy in a subject in need thereof, comprising administering a therapeutically effective amount of an inhibitor selected from the group consisting of an EZH1 inhibitor, an EZH2 inhibitor and an EZH1/2 dual inhibitor to the patient.

(13) The method according to (12), wherein the inhibitor is an EZH1/2 dual inhibitor.

(14) The method according to (12), wherein the inhibitor is a compound selected from N-[(1,2-dihydro-4,6-dimethyl-2-oxo-3-pyridinyl)methyl]-3-methyl-1-[(1S)-1-methylpropyl]-6-[6-(1-piperazinyl)-3-pyridinyl]-1H-indole-4-carboxamide, N-((4,6-dimethyl-2-oxo-1,2-dihydropyridin-3-yl)methyl)-5-(ethyl(tetrahydro-2H-piran-4-yl)amino)-4-methyl-4'-(morpholinomethyl)-[1,1'-biphenyl]-3-carboxamide, (2R)-7-bromo-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide, and (2R)-7-chloro-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide, or a pharmaceutically acceptable salt thereof.

(15) The method according to (12) or (13), wherein the inhibitor is (2R)-7-bromo-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide, or (2R)-7-chloro-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide, or a pharmaceutically acceptable salt thereof.

(16) The method according to (12) or (13), wherein the inhibitor is (2R)-7-bromo-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide, or a pharmaceutically acceptable salt thereof.

(17) The method according to (12) or (13), wherein the inhibitor is (2R)-7-chloro-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide, or a pharmaceutically acceptable salt thereof.

(18) The method according to (12) or (13), wherein the inhibitor is (2R)-7-chloro-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide p-toluene sulfonate.

(19) A method for treating HTLV-1-associated myelopathy in a subject in need thereof, including administering a therapeutically effective amount of a compound selected form N-[(1,2-dihydro-4,6-dimethyl-2-oxo-3-pyridinyl)methyl]-3-methyl-1-[(1S)-1-methylpropyl]-6-[6-(1-piperazinyl)-3-pyridinyl]-1H-indole-4-carboxamide, N-((4,6-dimethyl-2-oxo-1,2-dihydropyridin-3-yl)methyl)-5-(ethyl(tetrahydro-2H-piran-4-yl)amino)-4-methyl-4'-(morpholinomethyl)-[1,1'-biphenyl]-3-carboxamide, (2R)-7-bromo-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide and (2R)-7-chloro-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide, or a pharmaceutically acceptable salt thereof, to the subject.

(20) The method according to (19), wherein a therapeutically effective amount of (2R)-7-bromo-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide, or a pharmaceutically acceptable salt thereof is administered to the subject.

(21) The method according to (19), wherein a therapeutically effective amount of (2R)-7-chloro-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide, or a pharmaceutically acceptable salt thereof is administered to the subject.

(22) The method according to (19), wherein a therapeutically effective amount of (2R)-7-chloro-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide p-toluene sulfonate is administered to the subject.

(23) Use of an inhibitor selected from the group consisting of an EZH1 inhibitor, an EZH2 inhibitor and an EZH1/2 dual inhibitor, for the manufacture of a medicament for use in treating HTLV-1-associated myelopathy.

(24) Use according to (23), wherein the inhibitor is an EZH1/2 dual inhibitor.

(25) Use according to (23), wherein the inhibitor is a compound selected from

N-[(1,2-dihydro-4,6-dimethyl-2-oxo-3-pyridinyl)methyl]-3-methyl-1-[(1S)-1-methylpropyl]-6-[6-(1-piperazinyl)-3-pyridinyl]-1H-indole-4-carboxamide, N-((4,6-dimethyl-2-oxo-1,2-dihydropyridin-3-yl) methyl)-5-(ethyl(tetrahydro-2H-piran-4-yl)amino)-4-methyl-4'-(morpholinomethyl)-[1,1'-biphenyl]-3-carboxamide, (2R)-7-bromo-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide, and (2R)-7-chloro-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide, or a pharmaceutically acceptable salt thereof.

(26) Use according to (23) or (24), wherein the inhibitor is (2R)-7-bromo-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide, or (2R)-7-chloro-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide, or a pharmaceutically acceptable salt thereof.

(27) Use according to (23) or (24), wherein the inhibitor is (2R)-7-bromo-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide, or a pharmaceutically acceptable salt thereof.

(28) Use according to (23) or (24), wherein the inhibitor is (2R)-7-chloro-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide, or a pharmaceutically acceptable salt thereof.

(29) Use according to (23) or (24), wherein the inhibitor is (2R)-7-chloro-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide p-toluene sulfonate.

(30) Use of a compound selected from

N-[(1,2-dihydro-4,6-dimethyl-2-oxo-3-pyridinyl) methyl]-3-methyl-1-[(1S)-1-methylpropyl]-6-[6-(1-piperazinyl)-3-pyridinyl]-1H-indole-4-carboxamide, N-((4,6-dimethyl-2-oxo-1,2-dihydropyridin-3-yl) methyl)-5-(ethyl(tetrahydro-2H-piran-4-yl)amino)-4-methyl-4'-(morpholinomethyl)-[1,1'-biphenyl]-3-carboxamide, (2R)-7-bromo-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide, and (2R)-7-chloro-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide, or a pharmaceutically acceptable salt thereof, for production of a medicament for treating HTLV-1-associated myelopathy.

(31) Use according to (30) of (2R)-7-bromo-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide, or a pharmaceutically acceptable salt thereof.

(32) Use according to (30) of (2R)-7-chloro-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide, or a pharmaceutically acceptable salt thereof.

(33) Use according to (30) of (2R)-7-chloro-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide p-toluene sulfonate.

BRIEF DESCRIPTION OF DRAWINGS

FIG. 2 shows that compound A and compound B (defined later), which are EZH1/2 dual inhibitors, inhibit autoproliferation activity of PBMC (characteristically seen in HAM) in the absence of any stimulation.

FIG. 3 shows that E7438 and GSK126, which are EZH2 inhibitors, inhibit autoproliferation activity of PBMC (characteristically seen in HAM) in the absence of any stimulation.

FIG. 6 shows that EZH1/2 dual inhibitors, compound A and compound B, each reduce the viability of HTLV-1 infected cells established from the cerebrospinal fluid of a HAM patient.

FIG. 7 shows that EZH1/2 dual inhibitors, compound A and compound B, each reduce the viability of HTLV-1 infected cells established from the cerebrospinal fluid of a HAM patient, in a concentration-dependent manner.

DETAILED DESCRIPTION OF THE INVENTION

Figure 1:
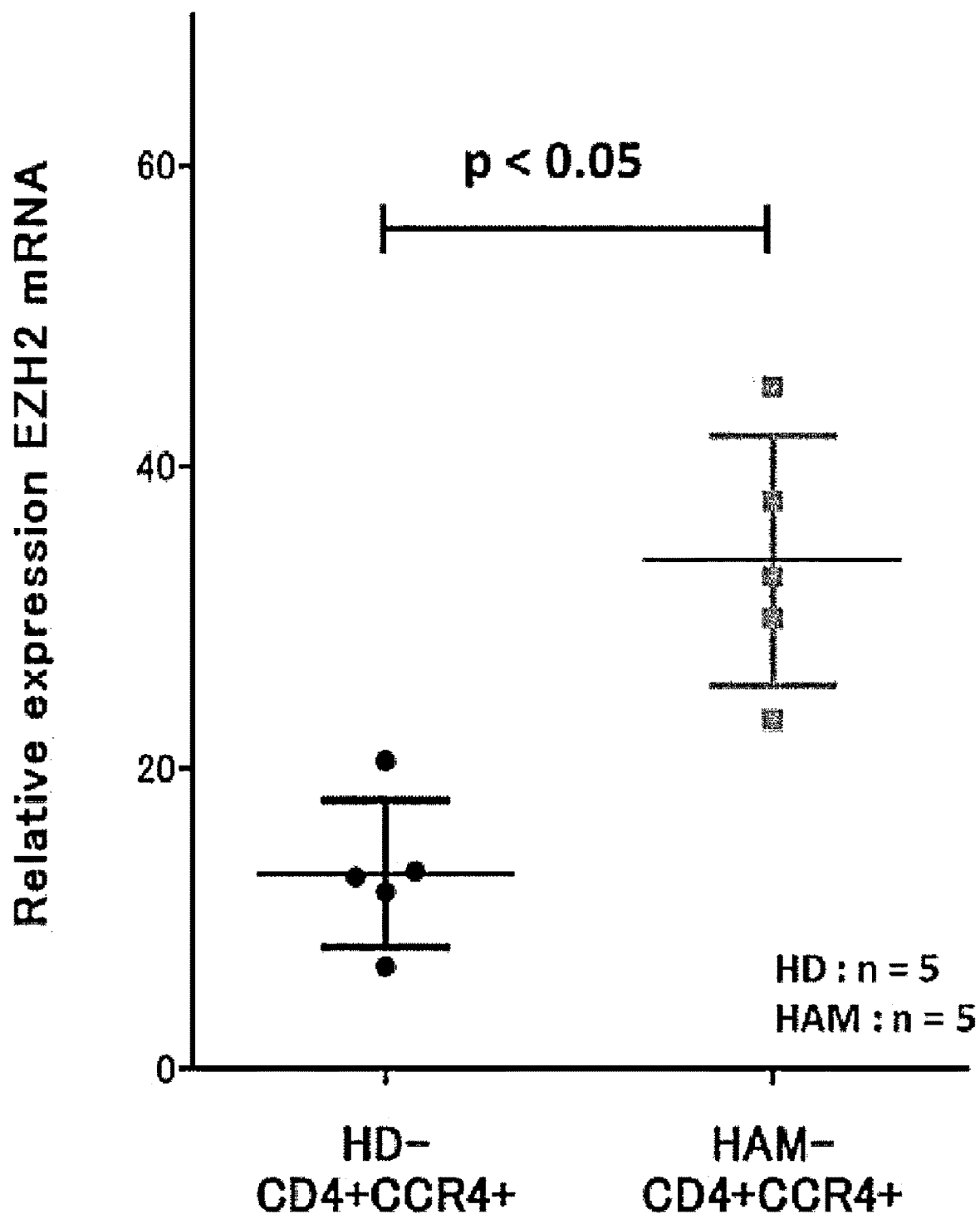
FIG. 1 shows that the level of EZH2 gene expression is higher in peripheral blood mononuclear cells (PBMC) taken from the peripheral blood of a HAM patient than in PBMC of a healthy person.

In the specification, the term "subject" refers to a mammal, particularly a human.

In the specification, the term "HTLV-1-associated myelopathy" (hereinafter sometimes referred to as "HAM") refers to a disease associated with chronic progressive spastic spinal paralysis, and diagnosed by a doctor in accordance with the WHO guidelines (Osame M. Review of WHO Kagoshima meeting and diagnostic guidelines for HAM/TSP. In: Blattner W, ed., Human Retrovirology: HTLV., New York, N.Y., USA: Raven Press; 1990: 191-197).

HAM is developed in part of the persons infected with human T lymphophilic virus type 1 (HTLV-1). In HAM, a chronic inflammatory process occurs in the spinal cord, particularly in and around the lower midthorax. In a spinal cord lesion of HAM, it has been clinically found that cellular immune response persistently occurs.

From in-situ PCR analysis for HTLV-1 infected cells in a spinal cord lesion of HAM, HTLV-1 infected cells are found only in infiltrative T cells and not found in the peripheral nerve cells or glial cells. From pathological analysis for the spinal cord lesion of HAM, it is shown that the cells mainly constituting infiltrative inflammatory cells are CD4 positive cells containing HTLV-1 infected cells, which appear in the early stage of the disease; however, which are replaced with CD8 positive cells as the disease progresses. From this, HAM is not considered as a simple infectious disease of the nerve but considered that immune response mainly mediated by infiltrated HTLV-1 infected T cells becomes out of control, with the result that a chronic inflammatory lesion is formed and/or maintained as a main pathological condition.

Adult T-cell leukemia lymphoma (ATL) is a disease developed in part of the HTLV-1 infected persons. It is known that ATL is a malignant tumor (cancer) derived from HTLV-1 infected cells and completely different from HAM. HTLV-1 infected cells are considered CD4+CD25+CCR4+ T cells not only in HAM but also ATL. In HAM, in CD4+CD25+CCR4+ T cells, expression of Foxp3 decreases and production of INF-γ is increased (expression of HTLV-1 tax is also high); whereas, regulatory T cells (Treg) are suppressed. In contrast, in ATL, in CD4+CD25+CCR4+ T cells, expression of Foxp3 increases (without HTLV-1 tax expression) and the T cells fall in immunosuppressive condition. Besides this, Treg function increases. Cellular immune deficiency clinically observed in ATL is explained by this phenomenon.

As described above, in HAM, immune response excessively occurs to form a chronic inflammatory lesion, which is a cause of HAM; whereas, in ATL, immune response is conversely suppressed.

In short, onset mechanisms of HAM and ATL are opposite as described above and the cell components involved therein mutually differ (Araya N., et al., Viruses, 3: 1532-1548, 2010).

The present inventors found that production of an immunosuppressive cytokine, IL-10, is increased by treating HAM patient-derived PBMC with an EZH1/2 dual inhibitor. The present inventors also found that if HAM patient-derived PMBC is treated with an EZH2 inhibitor or an EZH1/2 dual inhibitor, autoproliferation activity of the PMBC can be suppressed. The present inventors further found that if HTLV-1 infected cells established from the cerebrospinal fluid of a HAM patient are treated with an EZH1/2 dual inhibitor, the viability of cells is reduced and apoptosis of cells is induced.

Autoproliferation activity of HAM patient-derived PBMC was more effectively suppressed by an EZH1/2 dual inhibitor than an EZH2 inhibitor. Since the inhibitory effect against enzyme activity of EZH2 is equivalent but the effect of EZH1/2 dual inhibitor is high, it was found that the inhibition against the activity of EZH1 is also important for suppressing autoproliferation activity of HAM patient-derived PMBC.

Thus, according to the present invention, there is provided a pharmaceutical composition comprising an inhibitor selected from the group consisting of an EZH1 inhibitor, an EZH2 inhibitor and an EZH1/2 dual inhibitor as an active ingredient, for use in treating HTLV-1-associated myelopathy.

According to the present invention, there is provided a pharmaceutical composition comprising an EZH1 inhibitor as an active ingredient, for use in treating HTLV-1-associated myelopathy.

According to the present invention, there is provided a pharmaceutical composition comprising an EZH2 inhibitor as an active ingredient, for use in treating HTLV-1-associated myelopathy.

According to the present invention, there is also provided a pharmaceutical composition comprising an EZH1/2 dual inhibitor as an active ingredient, for use in treating HTLV-1-associated myelopathy.

The pharmaceutical composition of the present invention may further comprise an excipient.

Examples of the EZH1 inhibitor that can be used in the present invention include, but are not particularly limited to, (2R)-7-bromo-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide, (2R)-7-chloro-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide and pharmaceutically acceptable salts of these.

Examples of the EZH2 inhibitor that can be used in the present invention include, but are not particularly limited to, N-[(1,2-dihydro-4,6-dimethyl-2-oxo-3-pyridinyl) methyl]-3-methyl-1-[(1S)-1-methylpropyl]-6-[6-(1-piperazinyl)-3-pyridinyl]-1H-indole-4-carboxamide, N-((4,6-dimethyl-2-oxo-1,2-dihydropyridin-3-yl) methyl)-5-(ethyl(tetrahydro-2H-piran-4-yl)amino)-4-methyl-4'-(morpholinomethyl)-[1,1'-biphenyl]-3-carboxamide, (2R)-7-bromo-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide, (2R)-7-chloro-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide, and pharmaceutically acceptable salts of these. Examples of the EZH2 inhibitor that can be used in the present invention include (1S,2R,5R)-5-(4-aminoimidazo[4,5-c]pyridin-1-yl)-3-(hydroxymethyl)cyclopent-3-en-1,2-diol and a pharmaceutically acceptable thereof. Examples of the EZH2 inhibitor that can be used in the present invention further include N-[(6-methyl-2-oxo-4-propyl-1H-pyridin-3-yl)methyl]-1-propan-2-yl-6-[6-(4-propan-2-ylpiperazin-1-yl)pyridin-3-yl]indazole-4-carboxamide and a pharmaceutically acceptable salt thereof. Examples of the EZH2 inhibitor further include tazemetostat (EPZ-6438). Examples of the EZH2 inhibitor that can be used in the present invention further include N-[(1,2-dihydro-6-methyl-2-oxo-4-propyl-3-pyridinyl)methyl]-1-)1-methylethyl)-6-[2-(4-methyl-1-piperazinyl)-4-pyridinyl]-1H-indazole-4-carboxamide and a pharmaceutically acceptable salt thereof. Examples of the EZH2 inhibitor that can be used in the present invention further include a variety of compounds described in Stazi, G. et al., Expert Opinion on Therapeutic Patents, 27: 7, 797-813, 2017. EZH2 inhibitors are developed in the world; for example, EZH2 inhibitors described in the following documents can be used in the present invention: WO2014/100646, WO2015/057859, WO2016/081523, WO2014/144747, WO2015/010078, WO2015/010049, WO2015/200650, WO2015/132765, WO2015/004618, WO2016/066697, WO2014/124418, WO2015/023915, WO2016/130396, WO2015/077193, WO2015/077194, WO2015/193768, WO2016/073956, WO2016/073903, WO2016/102493, WO2016/089804, WO2014/151369. In the present invention, the EZH2 inhibitor may further have an EZH1 inhibitory effect and may be, for example, an EZH1/2 dual inhibitor. For example, the aforementioned N-[(6-methyl-2-oxo-4-propyl-1H-pyridin-3-yl)methyl]-1-propan-2-yl-6-[6-(4-propan-2-ylpiperazin-1-yl)pyridin-3-yl]indazole-4-carboxamide and a pharmaceutically acceptable salt thereof can be an EZH1/2 dual inhibitor. In an embodiment of the present invention, both an EZH1 inhibitor and an EZH2 inhibitor may be administered for treating a patient with HTLV-1-associated myelopathy.

Examples of the EZH1/2 dual inhibitor that can be used in the present invention include, but are not particularly limited to, (2R)-7-bromo-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide, (2R)-7-chloro-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide, and pharmaceutically acceptable salts of these.

(2R)-7-Bromo-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide is disclosed in WO2015/141616, Example 15, and a compound having the following structure.

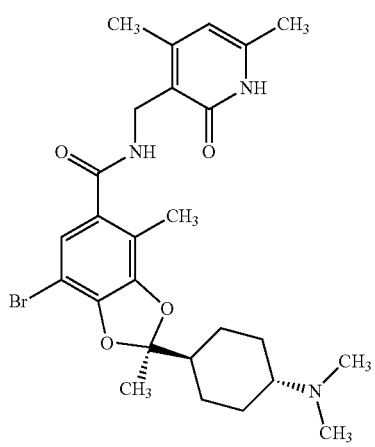

[Formula 1]

(2R)-7-Chloro-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide is disclosed in WO2015/141616, Example 35, and a compound having the following structure.

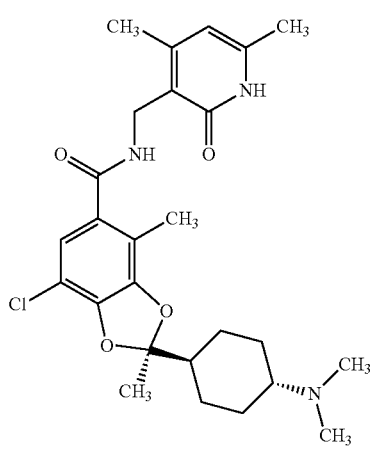

[Formula 2]

(2R)-7-Chloro-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide p-toluene sulfonate is disclosed in WO2015/141616, Example 80.

N-[(1,2-Dihydro-4,6-dimethyl-2-oxo-3-pyridinyl)methyl]-3-methyl-1-[(1S)-1-methylpropyl]-6-[6-(1-piperazinyl)-3-pyridinyl]-1H-indole-4-carboxamide is also referred to as GSK126, and disclosed in WO2011/140324, Example 270.

N-((4,6-Dimethyl-2-oxo-1,2-dihydropyridin-3-yl)methyl)-5-(ethyl(tetrahydro-2H-piran-4-yl)amino)-4-methyl-4'-(morpholinomethyl)-[1,1'-biphenyl]-3-carboxamide is also referred to as E7438 or EPZ-6438, and disclosed in WO2012/142504, Example 44.

In an embodiment of the present invention, an EZH1 inhibitor has an inhibitory effect against histone methyltransferase activity of human EZH1, and $IC_{50}$ thereof can be 1 μM or less, 500 nM or less, 400 nM or less, 300 nM or less, 200 nM or less, 150 nM or less, 100 nM or less, 90 nM or less, 80 nM or less, 70 nM or less, 60 nM or less, 50 nM or less, 40 nM or less, 30 nM or less, 20 nM or less, 15 nM or less, or 10 nM or less. The value $IC_{50}$ can be determined based on the method described in, for example, WO2015/141616, Test Example 1; for example, by detecting the inhibitory effect against the activity of EZH1 to transfer S-adenosyl methionine labeled with tritium to a peptide having an EZH1 target sequence (for example, a sequence of 12th to 40th amino acids of a human histone H3 protein; as to the amino acid sequence of the human histone H3 protein, see, for example, the sequence registered under GenBank registration number: CAB02546.1). The methyltransferase activity of EZH1 can be measured by using a PRC2-EZH1 complex.

In an embodiment of the present invention, an EZH2 inhibitor has an inhibitory effect against histone methyltransferase activity of human EZH2, and $IC_{50}$ thereof can be 1 μM or less, 500 nM or less, 400 nM or less, 300 nM or less, 200 nM or less, 150 nM or less, 100 nM or less, 90 nM or less, 80 nM or less, 70 nM or less, 60 nM or less, 50 nM or less, 40 nM or less, 30 nM or less, 20 nM or less, 15 nM or less, or 10 nM or less. The value $IC_{50}$ can be determined based on the method described in, for example, WO2015/141616, Test Example 2; for example, by detecting the inhibitory effect against the activity of EZH2 to transfer S-adenosyl methionine labeled with tritium to a peptide having an EZH2 target sequence (for example, a sequence of 12th to 40th amino acids of a human histone H3 protein; as to the amino acid sequence of the human histone H3 protein, see, for example, the sequence registered under GenBank registration number: CAB02546.1). EZH2 methyltransferase activity can be measured by using a PRC2-EZH2 complex.

In an embodiment of the present invention, an EZH1/2 dual inhibitor has an inhibitory effect against histone methyltransferase activity of human EZH1, and $IC_{50}$ thereof can be 1 μM or less, 500 nM or less, 400 nM or less, 300 nM or less, 200 nM or less, 150 nM or less, 100 nM or less, 90 nM or less, 80 nM or less, 70 nM or less, 60 nM or less, 50 nM or less, 40 nM or less, 30 nM or less, 20 nM or less, 15 nM or less, or 10 nM or less, and, has an inhibitory effect against histone methyltransferase activity of human EZH2, and $IC_{50}$ thereof can be 1 μM or less, 500 nM or less, 400 nM or less, 300 nM or less, 200 nM or less, 150 nM or less, 100 nM or less, 90 nM or less, 80 nM or less, 70 nM or less, 60 nM or less, 50 nM or less, 40 nM or less, 30 nM or less, 20 nM or less, 15 nM or less, or 10 nM or less. The values $IC_{50}$ for EZH1 and EZH2 each can be determined as mentioned above.

In an embodiment of the present invention, $GI_{50}$ of an EZH1 inhibitor against HCT-4 cell line established from a patient with HTLV-1-associated myelopathy can be 1 μM or less, 500 nM or less, 400 nM or less, 300 nM or less, 200 nM or less, 150 nM or less, 100 nM or less, 90 nM or less, 80 nM or less, 70 nM or less, 60 nM or less, 50 nM or less, 40 nM or less, 30 nM or less, 20 nM or less, 15 nM or less, or 10 nM or less. In the specification, "$GI_{50}$" refers to the concentration of a drug required for attaining a half of a maximum growth inhibitory activity of the drug.

In an embodiment of the present invention, $GI_{50}$ of an EZH2 inhibitor against HCT-4 cell line established from a patient with HTLV-1-associated myelopathy can be 1 µM or less, 500 nM or less, 400 nM or less, 300 nM or less, 200 nM or less, 150 nM or less, 100 nM or less, 90 nM or less, 80 nM or less, 70 nM or less, 60 nM or less, 50 nM or less, 40 nM or less, 30 nM or less, 20 nM or less, 15 nM or less, or 10 nM or less.

In an embodiment of the present invention, $GI_{50}$ of an EZH1/2 dual inhibitor against HCT-4 cell strain established from a patient with HTLV-1-associated myelopathy can be 1 µM or less, 500 nM or less, 400 nM or less, 300 nM or less, 200 nM or less, 150 nM or less, 100 nM or less, 90 nM or less, 80 nM or less, 70 nM or less, 60 nM or less, 50 nM or less, 40 nM or less, 30 nM or less, 20 nM or less, 15 nM or less, or 10 nM or less.

A compound of the present invention can be a pharmaceutically acceptable salt thereof, if desired. The pharmaceutically acceptable salt refers to a salt, which does not have significant toxicity and can be used as a medicament. The compound of the present invention has a basic group, and thus, formed into a salt by reacting it with an acid.

Examples of a salt based on a basic group include hydrohalides such as a hydrofluoric acid salt, a hydrochloride, a hydrobromide and a hydroiodide; inorganic acid salts such as nitrate, perchlorate, sulfate and phosphate; $C_1$-$C_6$ alkyl sulfonates such as methanesulfonate, trifluoromethanesulfonate and ethanesulfonate; aryl sulfonates such as benzene sulfonate and p-toluene sulfonate; organic acid salts such as an acetate, a malate, a fumarate, a succinate, citrate, ascorbate, tartrate, borate, adipate and maleate; and amino acid salts such as a glycine salt, a lysine salt, an arginine salt, an ornithine salt, a glutamate and an aspartate.

A pharmaceutically acceptable salt of a compound of the present invention sometimes takes up a water molecule and changes into a hydrate when it is left in the air or reprecipitated. Such a hydrate is also included in the salt of the present invention.

A pharmaceutically acceptable salt of a compound of the present invention sometimes absorbs a solvent and changes into as a solvate when it is left in a solvent or reprecipitated. Such a solvate is also included in the salt of the present invention.

The present invention includes a compound, which is converted into compound A or compound B serving as an active ingredient of the pharmaceutical composition of the present invention, through a reaction with, e.g., an enzyme or gastric acid in the in-vivo physiological conditions, in other words, a compound converted into compound A or compound B by, e.g., an enzymatic oxidation, reduction or hydrolysis, or "a pharmaceutically acceptable prodrug compound", which is to be converted into compound A or compound B by hydrolysis with, e.g., gastric acid.

The compound of the present invention or a pharmaceutically acceptable salt thereof can be isolated and purified by a method known in the art, such as extraction, precipitation, distillation, chromatography, separation by precipitation and reprecipitation.

The compound of the present invention may contain an atomic isotope as at least one atom constituting the compound in a non-naturally occurring ratio. As the atomic isotope, e.g., deuterium ($^2$H), tritium ($^3$H), iodine-125 ($^{125}$I) or carbon-14 ($^{14}$C) is mentioned. The compound can be labelled with a radioactive isotope such as tritium ($^3$H), iodine-125 ($^{125}$I) or carbon-14 ($^{14}$C). The compound labeled with a radioactive isotope is useful as a therapeutic or prophylactic agent, a research reagent such as an assay reagent, and a diagnostic agent such as an in-vivo diagnostic imaging agent. All isotopic variants of a compound of the present invention are included in the range of the present invention irrespective of whether they are radioactive or not.

A compound of the present invention or a pharmaceutically acceptable salt thereof can be administered by various administration methods. The administration methods include, oral administration, e.g., administration of tablets, capsules, granules, emulsions, pills, powders and syrups (liquid formulation), or parenteral administration, e.g., administration by injections (intravenous, intramuscle, subcutaneous or intraperitoneal administration), drip agents and suppositories (rectal administration). These various preparations can be prepared by using a main drug and additives which are ordinarily used in the technical field of medicinal preparation, such as an excipient, a binder, a disintegrant, a lubricant, a flavoring agent, a solubilizer, a suspending agent and a coating agent.

If tablets are prepared, examples of a carrier that can be used include an excipient such as lactose, white sugar, sodium chloride, glucose, urea, starch, calcium carbonate, kaolin, crystalline cellulose and silica; a binder such as water, ethanol, propanol, simple syrup, a glucose solution, a starch solution, a gelatin solution, carboxymethylcellulose, shellac, methyl cellulose, potassium phosphate and polyvinyl pyrrolidone; a disintegrant such as dry starch, sodium alginate, agar powder, laminaran powder, sodium hydrogen carbonate, calcium carbonate, polyoxyethylene sorbitan fatty acid ester, sodium lauryl sulfate, monoglyceryl stearate, starch and lactose; a collapse suppressor such as white sugar, stearin, cocoa butter and hydrogenated oil; an absorption promoter such as a quaternary ammonium salt and sodium lauryl sulfate; a moisturizer such as glycerin and starch; an adsorbent such as starch, lactose, kaolin, bentonite and colloidal silicic acid; and a lubricant such as purified talc, stearate, oxalic acid powder and polyethylene glycol. If necessary, tablets coated with an ordinary film such as sugar coated tablets, gelatin encapsulated tablets, enteric coated tablets and film coated tablets or double-layer tablets and multilayer tablets can be used.

If pills are prepared, examples of a carrier thereof that can be used include an excipient such as glucose, lactose, cocoa butter, starch, hydrogenated vegetable oil, kaolin and talc; a binder such as gum Arabic, tragacanth powder, gelatin and ethanol; and a disintegrant such as laminaran and agar.

If a suppository is prepared, a wide variety of substances known in this field can be used as a carrier. Examples of the carrier include polyethylene glycol, cocoa butter, a higher alcohol, an ester of a higher alcohol, gelatin and semi-synthetic glyceride.

If an injection is prepared, a liquid formulation, an emulsion or a suspending agent can be used. The liquid formulation, emulsion or suspending agent is preferably sterilized and isotonic to blood. A solvent to be used for producing the liquid formulation, emulsion or suspending agent is not particularly limited as long as it is used as a diluent for medical use. Examples of the solvent include water, ethanol, propylene glycol, an ethoxylated isostearyl alcohol, a polyoxylated isostearyl alcohol and a polyoxyethylene sorbitan fatty acid ester. Note that, in this case, a salt, glucose or glycerin may be contained in a sufficient amount for preparing an isotonic solution, and, e.g., a solubilizer, a buffer and a soothing agent, which are ordinarily used, may be contained.

The aforementioned preparation, if necessary, may contain, e.g., a colorant, a preservative, an aroma chemical, a flavor agent and a sweetener, and another medical drug can be further contained.

The amount of a compound serving as an active ingredient of the aforementioned preparation is not particularly limited and appropriately selected from a wide range. The amount is usually 0.5 to 70 wt %, preferably 1 to 30 wt % of the whole composition (preparation).

The use amount (dosage) of the compound varies depending on the symptom and age of a patient (warm-blooded animal, particularly human). In the case of oral administration, the upper limit of the dosage is 2000 mg (preferably, 100 mg) and the lower limit is 0.1 mg (preferably, 1 mg, further preferably, 10 mg) per day per adult. Administration can be made 1 to 6 times per day depending on the symptom.

The pharmaceutical composition of the present invention can be used in combination with another HAM therapeutic agent. Examples of the HAM therapeutic agent to be used in combination include, but are not particularly limited to, adrenocortical hormone, prednisolone, interferon-α, azathioprine, salazosulfapyridine, ascorbic acid, pentoxifylline, *Lactobacillus casei* Shirota (Yakult 400), erythromycin, mizoribine, fosfomycin, griseall, human immunoglobulin, danazol and eperisone hydrochloride.

Accordingly, in the present invention, there is provided a pharmaceutical composition comprising an inhibitor selected from the group consisting of an EZH1 inhibitor, an EZH2 inhibitor and an EZH1/2 dual inhibitor as an active ingredient, for use in treating HTLV-1-associated myelopathy, and to be used in combination with another HAM therapeutic agent as mentioned above. In the present invention, there is provided a combined drug comprising an inhibitor selected from the group consisting of an EZH1 inhibitor, an EZH2 inhibitor and an EZH1/2 dual inhibitor and at least one of the HAM therapeutic agents mentioned above, for use in treating HTLV-1-associated myelopathy.

According to the present invention, there is provided use of an inhibitor selected from the group consisting of an EZH1 inhibitor, an EZH2 inhibitor and an EZH1/2 dual inhibitor, for the manufacture of a medicament for use in treating HTLV-1-associated myelopathy.

According to the present invention, there is provided use of an EZH1 inhibitor for the manufacture of a medicament for use in treating HTLV-1-associated myelopathy.

According to the present invention, there is provided use of an EZH2 inhibitor for the manufacture of a medicament for use in treating HTLV-1-associated myelopathy.

According to the present invention, there is provided use of an EZH1/2 dual inhibitor for the manufacture of a medicament for use in treating HTLV-1-associated myelopathy.

According to the present invention, there is provided use of a compound selected from (2R)-7-bromo-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide, and (2R)-7-chloro-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide and pharmaceutically acceptable salts of these for the manufacture of a medicament for use in treating HTLV-1-associated myelopathy.

According to the present invention, there is provided use of a compound selected from N-[(1,2-dihydro-4,6-dimethyl-2-oxo-3-pyridinyl)methyl]-3-methyl-1-[(1S)-1-methylpropyl]-6-[6-(1-piperazinyl)-3-pyridinyl]-1H-indole-4-carboxamide, N-((4,6-dimethyl-2-oxo-1,2-dihydropyridin-3-yl)methyl)-5-(ethyl(tetrahydro-2H-piran-4-yl)amino)-4-methyl-4'-(morpholinomethyl)-[1,1'-biphenyl]-3-carboxamide, (2R)-7-bromo-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide, and (2R)-7-chloro-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide, and pharmaceutically acceptable salts of these, for the manufacture of a medicament for use in treating HTLV-1-associated myelopathy.

In a preferable embodiment of the present invention, as a pharmaceutically acceptable salt of EHZ1/2 dual inhibitor, i.e., (2R)-7-chloro-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide, (2R)-7-chloro-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide p-toluene sulfonate, can be used, for treatment of HTLV-1-associated myelopathy or the manufacture of a medicament for treating HTLV-1-associated myelopathy.

According to the present invention, there is provided a method for treating HTLV-1-associated myelopathy in a subject suffering from HTLV-1-associated myelopathy, including administering, to the subject, a therapeutically effective amount of an inhibitor selected from the group consisting of an EZH1 inhibitor, an EZH2 inhibitor and an EZH1/2 dual inhibitor.

According to the present invention, there is provided a method for treating HTLV-1-associated myelopathy in a subject suffering from HTLV-1-associated myelopathy, including administering, to the subject, a therapeutically effective amount of a compound selected from N-[(1,2-dihydro-4,6-dimethyl-2-oxo-3-pyridinyl)methyl]-3-methyl-1-[(1S)-1-methylpropyl]-6-[6-(1-piperazinyl)-3-pyridinyl]-1H-indole-4-carboxamide, N-((4,6-dimethyl-2-oxo-1,2-dihydropyridin-3-yl)methyl)-5-(ethyl(tetrahydro-2H-piran-4-yl)amino)-4-methyl-4'-(morpholinomethyl)-[1,1'-biphenyl]-3-carboxamide, (2R)-7-bromo-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide, and (2R)-7-chloro-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide and pharmaceutically acceptable salts of these.

According to the present invention, there is provided an immunosuppressant comprising an inhibitor selected from the group consisting of an EZH1 inhibitor, an EZH2 inhibitor and an EZH1/2 dual inhibitor.

According to the present invention, there is provided an inhibitor selected from the group consisting of an EZH1 inhibitor, an EZH2 inhibitor and an EZH1/2 dual inhibitor for use in suppressing immunity.

According to the present invention, there is provided use of an inhibitor selected from the group consisting of an EZH1 inhibitor, an EZH2 inhibitor and an EZH1/2 dual inhibitor, for the manufacture of a medicament for use in suppressing immunity. According to the present invention, there is provided a method for suppressing immunity in a subject in need thereof, including administering, to the subject, a therapeutically effective amount of an inhibitor selected from the group consisting of an EZH1 inhibitor, an EZH2 inhibitor and an EZH1/2 dual inhibitor.

In each of the embodiments regarding suppression of immunity, an inhibitor as mentioned above can be administered to a subject suffering from HTLV-1-associated myelopathy. In each of the embodiments, suppression of immunity can be suppression of inflammation enhanced in a subject suffering from HTLV-1-associated myelopathy. In each of the embodiments, the aforementioned inhibitors are mentioned as the EZH1 inhibitor, EZH2 inhibitor and EZH1/2 dual inhibitor and can be used in the present invention.

According to the present invention, there is also provided a pharmaceutical composition comprising an inhibitor selected from the group consisting of an EZH1 inhibitor, an EZH2 inhibitor and an EZH1/2 dual inhibitor for use in enhancing the yield of IL-10 in a subject. According to the present invention, there is provided an inhibitor selected from the group consisting of an EZH1 inhibitor, an EZH2 inhibitor and an EZH1/2 dual inhibitor for use in enhancing the yield of IL-10. According to the present invention, there is provided use of an inhibitor selected from the group consisting of an EZH1 inhibitor, an EZH2 inhibitor and an EZH1/2 dual inhibitor, for the manufacture of a medicament for use in enhancing the yield of IL-10. According to the present invention, there is provided a method for enhancing of the yield of IL-10 in a subject in need thereof, including administering, to the subject, a therapeutically effective amount of an inhibitor selected from the group consisting of an EZH1 inhibitor, an EZH2 inhibitor and an EZH1/2 dual inhibitor.

In each of the embodiments regarding enhancement of IL-10 yield, an inhibitor as mentioned above can be administered to, for example, a subject suffering from HTLV-1-associated myelopathy. In each of the embodiments, the inhibitors as mentioned above can be used as the EZH1 inhibitor, EZH2 inhibitor and EZH1/2 dual inhibitor in the present invention.

According to the present invention, there is also provided a pharmaceutical composition comprising an inhibitor selected from the group consisting of an EZH1 inhibitor, an EZH2 inhibitor and an EZH1/2 dual inhibitor, for use in suppressing proliferation activity of PBMC in a subject (for example, a subject suffering from HTLV-1-associated myelopathy). According to the present invention, there is provided an inhibitor selected from the group consisting of an EZH1 inhibitor, an EZH2 inhibitor and an EZH1/2 dual inhibitor for use in suppressing proliferation activity of PBMC in a subject (for example, a subject suffering from HTLV-1-associated myelopathy). According to the present invention, there is provided use of an inhibitor selected from the group consisting of an EZH1 inhibitor, an EZH2 inhibitor and an EZH1/2 dual inhibitor, for the manufacture of a medicament for use in suppressing proliferation activity of PBMC in a subject (for example, a subject suffering from HTLV-1-associated myelopathy). According to the present invention, there is provided a method for suppressing proliferation activity of PBMC in a subject (for example, a subject suffering from HTLV-1-associated myelopathy) in need thereof, including administering, to the subject, a therapeutically effective amount of an inhibitor selected from the group consisting of an EZH1 inhibitor, an EZH2 inhibitor and an EZH1/2 dual inhibitor. In the embodiment, the proliferation activity of PBMC can be HTLV-1 infected cell inductive self-proliferation activity. In the embodiment, the proliferation activity of PBMC can be autoproliferation activity in the absence of proliferation stimulation. In the embodiment, CD4+ single positive T cell and/or CD8+ single positive T cell can be included in PBMC. In the embodiment, CD4+CD25+CCR4+ T cell can be included in PBMC.

In each of these embodiments regarding suppression of PBMC proliferation activity, an inhibitor as mentioned above can be administered to, for example, a subject suffering from HTLV-1-associated myelopathy. In each of the embodiments, the inhibitors as mentioned above are mentioned as the EZH1 inhibitor, EZH2 inhibitor and EZH1/2 dual inhibitor and can be used in the present invention.

According to the present invention, there is provided a pharmaceutical composition comprising an inhibitor selected from the group consisting of an EZH1 inhibitor, an EZH2 inhibitor and an EZH1/2 dual inhibitor for use in inducing apoptosis of HTLV-1 infected cells. According to the present invention, there is provided an inhibitor selected from the group consisting of an EZH1 inhibitor, an EZH2 inhibitor and an EZH1/2 dual inhibitor for use in inducing apoptosis of HTLV-1 infected cells. According to the present invention, there is provided use of an inhibitor selected from the group consisting of an EZH1 inhibitor, an EZH2 inhibitor and an EZH1/2 dual inhibitor, for the manufacture of a medicament for use in inducing apoptosis of HTLV-1 infected cells. In the present invention, there is provided a method for inducing apoptosis of HTLV-1 infected cells in a subject (for example, a subject suffering from HTLV-1-associated myelopathy) in need thereof, including administering, to the subject, a therapeutically effective amount of an inhibitor selected from the group consisting of an EZH1 inhibitor, an EZH2 inhibitor and an EZH1/2 dual inhibitor.

In each of these embodiments regarding induction of apoptosis of HTLV-1 infected cells, HTLV-1 infected cells are present in the body of a subject suffering from HTLV-1-associated myelopathy. In each of these embodiments, an inhibitor as mentioned above can be administered to, for example, a subject suffering from HTLV-1-associated myelopathy. In each of the embodiments, inhibitors as mentioned above are mentioned as EZH1 inhibitor, EZH2 inhibitor and EZH1/2 dual inhibitor and can be used in the present invention.

EXAMPLES (2R)-7-bromo-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide will be referred to as compound A. Also, (2R)-7-chloro-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide will be referred to as compound B.

Compound A was synthesized in accordance with the description of WO2015/141616, Example 15. Compound B was synthesized in accordance with the description of WO2015/141616, Example 35. In the following Examples, compounds A and B thus synthesized were used.

Note that, compounds A and B inhibit enzyme activities of both EZH1 and EZH2 (WO2015/141616).

In the following Examples, HAM/TSP patients were diagnosed by a doctor in accordance with the WHO diagnostic criteria (Osame M. Review of WHO Kagoshima meeting and diagnostic guidelines for HAM/TSP In: Blattner W, ed. Human Retrovirology: HTLV. New York, N.Y., USA: Raven Press; 1990: 191-197).

Example 1: Increase of EZH2 Expression Level in HAM Cells

In this Example, the peripheral blood mononuclear cells (PBMC) obtained from HAM patients and PBMC obtained from healthy persons will be subjected to gene expression analysis to demonstrate that EZH2 expression level is elevated in the HAM patient-derived PMBC.

From the peripheral blood mononuclear cells (Peripheral Blood Mononuclear Cell: PBMC) separated from peripheral blood of 5 HAM patients, CD4+ cells were separated by use of a human CD4+ isolation kit (Miltenyi Biotec), and thereafter, CD4+CCR4+ cells were separated by use of Anti-mouse IgG1 MicroBeads (Miltenyi Biotec) to which an anti-CCR4 antibody (BD 551121) was bound. In the CD4+ CCR4+ cell fraction, HTLV-1 infected cells are contained. CD4+CCR4+ cells were separated in the same manner as above from PBMC of 5 healthy persons and used as a control group. From the CD4+CCR4+ cells separated, total RNA was obtained and cDNA was prepared by use of ReverTra Ace (Toyobo Co., Ltd). Using cDNA thus prepared, difference in gene expression between the HAM patient-derived CD4+CCR4+ cells and healthy person-derived CD4+CCR4+ cells was cyclopaedically analyzed by microarray analysis. As a result, it was found that EZH2 expression level differs. Then, the difference in EZH2 expression level was more specifically analyzed by Real time PCR. The primer set used for detection of EZH2 expressed was: EZH2#35-F: TGTGGATACTCCTCCAAGGAA and EZH2#35-R: GAGGAGCCGTCCTTTTTCA; the probe used herein was Universal ProbeLibrary #35 (Roche). A significance test was carried out in accordance with a paired t-test of GraphPad Prism6 (MDF). The results were as shown in FIG. 1.

As shown in FIG. 1, expression of EZH2 mRNA in the HAM patient-derived CD4+CCR4+ cells (HAM-CD4+ CCR4+) was significantly high, i.e., 2.6 times as high as in healthy person-derived CD4+CCR4+ cells (HD-CD4+ CCR4+). From the results, it was demonstrated that the EZH2 expression in HAM patient-derived infected cells is higher than the healthy person-derived cells.

Interestingly, the EZH2 expression level in CD4+ T cells other than HTLV-1 infected cells was high.

Example 2: Effect of EZH1/2 Dual Inhibitor on HAM

HAM patient-derived PBMC have a feature not seen in other PBMC in that the cells spontaneously proliferate by culturing them in the absence of any stimulation.

Then, using HAM patient-derived PBMC, the effect of the EZH1/2 dual inhibitor was examined. As the EZH1/2 dual inhibitor, compound A and compound B were used.

The effects of compound A and compound B were evaluated based on (1) autoproliferation activity; (2) change in yield of inflammatory suppression cytokine IL-10 (Example 3, later described); and (3) change in number of HTLV-1 infected cells (Example 4, later described) in HAM patient's PBMC. In the evaluation time, a group treated with DMSO and a group treated with prednisolone (PSL, 1 µg/ml) were used as controls. PSL having an inflammatory suppression action can suppress autoproliferation activity of the HAM patient's PBMC; however, PSL does not exhibit infected cell removal activity in this experimental system or clinical sites.

Suppressive Effects of Compound A and Compound B on Excessive Immune Response of HAM Patient-Derived PBMC PBMC taken from 8 HAM patients were suspended in culture mediums (RPMI1640 culture medium (wako) containing 10% FBS (GIBCO)), seeded in a 96-well round-bottom plate in a ratio of $1\times10^5$ cells per well (3 wells were used for each concentration), and compound A or compound B was added so as to provide a final concentration of 1, 10, 100 or 1000 nM. Culture was carried out at 37° C. in 5% $CO_2$ conditions for 6 days. The DMSO treatment group and the PSL (1 µg/mL) treatment group were used as controls. Day 6 after initiation of culture, 1 µCi $^3$H-thymidine was added to each well and culture was carried out at 37° C., in 5% $CO_2$ conditions for 16 hours. Thereafter, the cultured cells were allowed to adsorb to a glass filter (Printed Filtermat A, PerkinElmer) by a cell harvester (Tomtec MH3, PerkinElmer), dried and impregnated with solid scintillator Meltilex-A (PerkinElmer). The amount of the $^3$H-thymidine incorporated in the cells was measured by use of MicroBeta (WALLAC MicroBeta TriLux 1450-021) (Yamano et al., PLoS One. 2009, 4(8): e6517). Based on the average count of $^3$H-thymidine in the DMSO treatment group of HAM patients' PBMC as 100%, the relative values of the groups treated with compound A, compound B and PSL (1 µg/mL) were obtained by calculation, and then, an average value of 8 HAM patient cases was obtained. A significance test was carried out in accordance with the Friedman test of GraphPad Prism6 (MDF). The results were as shown in FIG. 2, upper panel.

As shown in FIG. 2, upper panel, both compound A and compound B suppressed autoproliferation activity of PBMC in all the eight HAM patient cases, in a concentration-dependent manner. Based on the average of all the cases used in the experiment, a statistically significant suppression effect was observed in either case of the treatment with compound A or compound B (100 nM or more). At this time, $GI_{50}$ of compound A was 73.0 nM and $GI_{50}$ of compound B was 33.9 nM. Thus, it was suggested that the EZH1/2 dual inhibitor has an effect of suppressing excessive immune response of HAM patient-derived PBMC.

The number of patients was increased to 16 and the same experiment as above was carried out. The results are shown in FIG. 2, lower panel. Based on the results of 16 HAM patients on spontaneous proliferation activity, $GI_{50}$ of compound A was 45.6 nM and $GI_{50}$ of compound B was 25.9 nM.

In either one of the experiments, as shown in the upper panel and lower panel of FIG. 2, even in a low concentration region of 100 nM or less, inhibitory actions of compound A and B against spontaneous proliferation activity of HAM patient-derived PMBC were observed.

Suppressive Effect of EZH2 Inhibitor on Excessive Immune Response of HAM Patient-Derived PBMC Effect on HAM patient-derived PBMC was checked in the same manner as in the above Example except that an EZH2 inhibitor was used in place of compounds A and B.

As the EZH2 inhibitor, GSK126 (CAS No.: 1346574-57-9) and E7438 (CAS No.: 1403254-99-8) were used. The concentration for treatment was 1, 10, 100, 1000 or 10000 nM in terms of final concentration. In the experiment, PBMC samples taken from the 8 persons before the number of cases increased in the above were used. The results were as shown in FIG. 3.

As shown in FIG. 3, it was confirmed that E7438 (FIG. 3, upper panel) and GSK126 (FIG. 3, lower panel) each suppress autoproliferation activity of HAM patient-derived PBMC. $GI_{50}$ of E7438 was 214.2 nM and $GI_{50}$ of GSK126 was 724.3 nM.

As described above, suppressive actions of E7438 and GSK126 against spontaneous proliferation activity of HAM patient-derived PBMC were observed in a low-concentration region of 1 µM or less.

The magnitudes of inhibitory effects of the EZH1/2 dual inhibitor and the EZH2 inhibitor used in this Example on enzyme activity of EZH2 are not significantly different. Accordingly, it is understood that not only inhibition of EZH2 but also inhibition of EZH1 has a strongly influence inhibitory effect on spontaneous proliferation activity of HAM patient-derived PBMC.

Example 3: Production of Inflammatory Suppressive Cytokine IL-10 Induced by EZH1/2 Dual Inhibitor The pathological condition of HAM is characterized by inflammation induced by PBMC. Thus, in this Example, the effect of an EZH1/2 dual inhibitor on release of a cytokine from PBMC was examined.

PBMC taken from 8 HAM patients were suspended in a culture medium (RPMI1640 culture medium containing 10% FBS), seeded in a 48-well plate in a ratio of $5\times10^5$ cells per well and a compound A or compound B was added so as to provide a final concentration of 1, 10, 100 or 1000 nM. The culture solution of 0.5 mL in total was cultured at 37° C. in 5% $CO_2$ conditions for 12 days. A group treated with DMSO and a group treated with PSL (1 µg/mL) were used as controls. Day 12 after initiation of the culture, the culture solution was centrifuged, and thereafter, the culture supernatant alone was recovered. The concentration of IL-10 in the culture supernatant was determined by use of the Cytokine Beads Array kit (BD Biosciences) and a flow cytometer FACSCantoII (BD Biosciences) (Yamauchi et al., J Infect Dis. 2015, 211 (2): 238-48). Based on the IL-10 concentration in the culture solution of the DMSO treatment group as 100%, changes in IL-10 concentration of culture solutions of groups treated with compound A and compound B different in concentration or a group treated with PSL (1 µg/mL) were compared. The significance test was carried out by using the Friedman test of GraphPad Prism6 (MDF). The results were as shown in FIG. 4.

Figure 4:
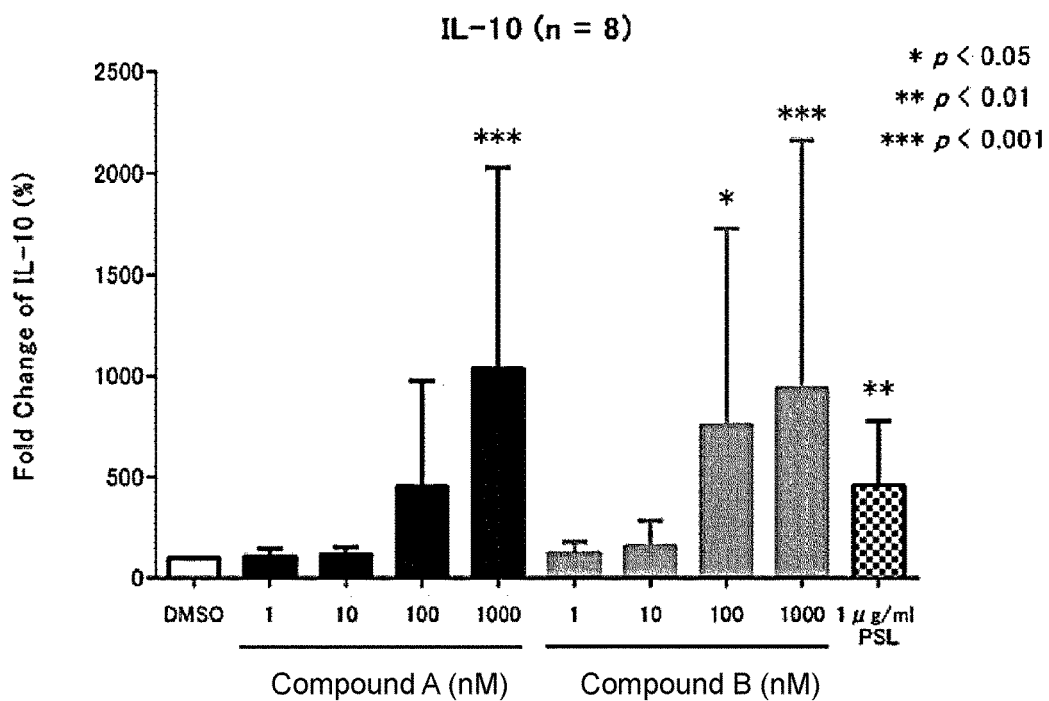
FIG. 4 shows that EZH1/2 dual inhibitors, compound A and compound B, each enhance release of an immunosuppressive cytokine, IL-10.

As shown in FIG. 4, the yield of IL-10 from PBMC was dramatically increased by each of compound A and compound B; and more specifically, it was found that the yield of the IL-10 production (acceleration) is the same or more even at a concentration of about 1/10 as low as PSL, which is known as an inflammatory suppression agent.

From the above, it was suggested that compound A and compound B act on HAM patient-derived PBMC and suppress inflammation, which is a main pathological condition of HAM.

In contrast, no significant change in yields of INF-α, TNF-α and IL-6 amount was observed.

HAM patient-derived PBMC has autoproliferation activity in the absence of any stimulation. The autoproliferation activity is conceivably produced by excessive response of the immune system caused by HAM infection cells. Example 3 demonstrated that an EZH1/2 dual inhibitor causes HAM patient-derived PBMC to produce IL-10 having an immunosuppressive action. The possibility that the EZH1/2 dual inhibitor might suppress excessive response of the immune system through IL-10 having an immunosuppressive action, thereby inhibiting spontaneous proliferation activity of PBMC, is suggested.

Example 4: Effect of EZH1/2 Dual Inhibitor on Removal of HTLV-1 Infected Cells from HAM Patient-Derived PMBC In this Example, whether or not an EZH1/2 dual inhibitor has an effect on removal of HTLV-1 infected cells causing HAM was examined.

PBMC taken from 8 HAM patients were suspended in a culture medium (RPMI1640 culture medium containing 10% FBS) and seeded in a 48-well plate in a ratio of $5\times10^5$ cells per well, and compound A or compound B was added so as to provide a final concentration of 1, 10, 100 or 1000 nM. The culture solution of 0.5 mL in total was cultured at 37° C. in 5% $CO_2$ conditions for 12 days. A group treated with DMSO and a group treated with PSL (1 µg/mL) were used as controls. Day 12 after initiation of culture, the culture solution was centrifuged, and thereafter, the cell suspension was recovered from each of the cultures carried out under different conditions and centrifuged. After the supernatant was removed, the cell pellet was subjected to genomic DNA extraction. The genome DNA extracted was subjected to real time PCR to measure HTLV-1 pro-viral load (infected cell rate) (Yamano et al., Blood. 2002, 99 (1): 88-94). Based on the HTLV-1 pro-viral load in cells, which were obtained by adding DMSO to each of the HAM patient's PBMC and culturing the PBMC, as 100%, the relative value of HTLV-1 pro-viral load in a group treated with compound A, compound B or PSL was calculated, and then, an average value of 8 HAM patient cases was obtained. The significance test was carried out by using the Friedman test of GraphPad Prism6 (MDF). The results were as shown in FIG. 5.

Figure 5:
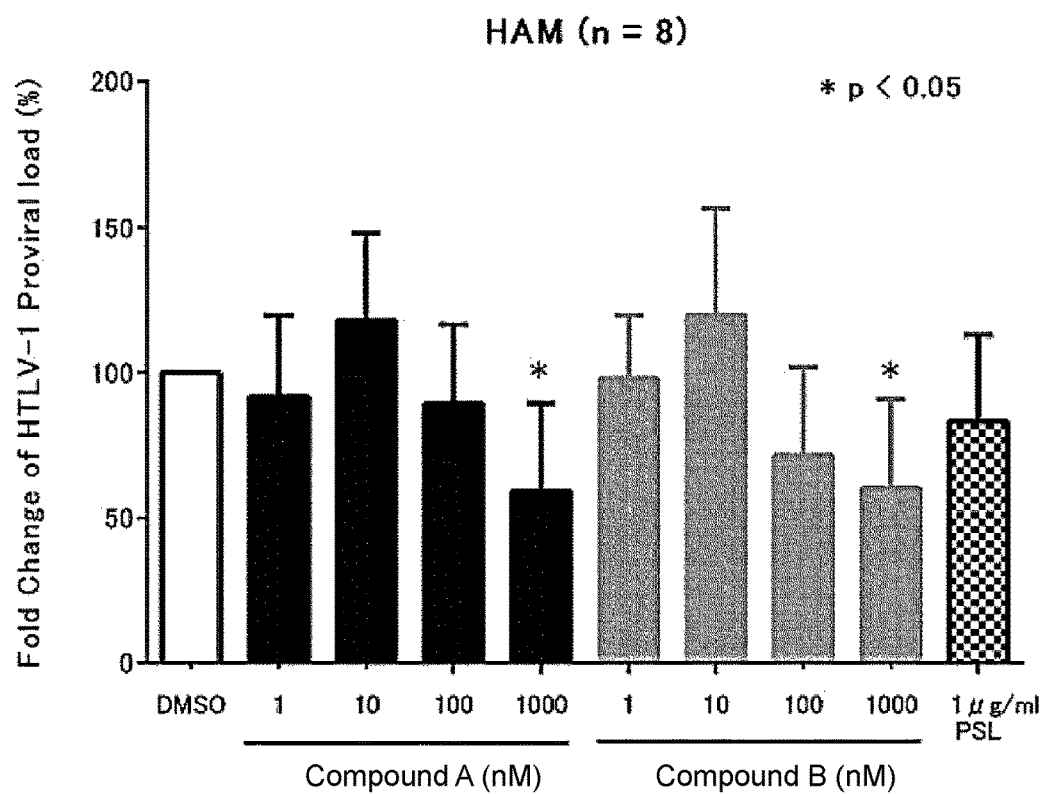
FIG. 5 shows that EZH1/2 dual inhibitors, compound A and compound B, each reduce HTLV-1 pro-viral load.

As shown in FIG. 5, it was found that HTLV-1 pro-viral load in the HAM patient's PBMC decreases by the treatment with compound A or compound B in 5 out of 8 cases. Based on the average value of all HAM patients used in the experiment, a significant reduction in pro-viral load was confirmed in the cases treated with 1000 nM compound A or compound B.

Example 5: Effect of EZH1/2 Dual Inhibitor on HTLV-1 Infected Cells

In this Example, effect of an EZH1/2 dual inhibitor on proliferation of a HTLV-1 infected cell line, which was established from the cerebrospinal fluid of a HAM patient, was examined.

HCT-4 and HCT-5, which were HTLV-1 infected cell lines established from the cerebrospinal fluid of HAM patients, were donated from a professor, Tatsufumi Nakamura of the Nagasaki International University. HCT-4 was cultured in RPMI1640 culture medium containing 10% FBS (GIBCO), a 1% penicillin-streptomycin solution (Wako) and 100 U/mL IL-2 (Cell Science & Technology Institute, Inc.); whereas HCT-5 was cultured by using 10% FBS, 1% penicillin-streptomycin solution, 1% L-glutamine (SIGMA) and 200 U/mL IL-2. HCT-4 ($3\times10^6$ cells) or HCT-5 ($2.5\times10^6$ cells) were seeded in a culture medium (20 mL) in a 75 $cm^2$-culture flask. DMSO was added and compound A or B was added so as to provide a final concentration of 1 µM and culture was carried out at 37° C. in 5% $CO_2$ conditions for 21 days while repeating subculture. In the subculture, a culture solution containing HCT-4 treated with DMSO so as to correspond to $3\times10^6$ cells, whereas a culture solution containing HCT-5 treated with DMSO so as to correspond to $2.5\times10^6$ cells were taken and each added to a new culture medium to obtain a final volume of 20 mL, and then, further compound A or B was added so as to obtain the same concentration as above. Day 7, 14 and 21 after initiation of culture, cells were recovered from the culture solution and the density of the cells was measured. In this manner, the effect of compound A or B on cell proliferation was examined. The density of cells was determined by seeding cultured cells in a 96-well plate in a volume of 100 µL per well, adding 10 μL of Cell counting kit-8 (CCK-8) (Dojindo Laboratories laboratory) per well, incubating the cells at 37° C. for 3 hours and measuring absorbance at 450 nm by a plate reader (iMark Microplate Reader, Biorad). The proliferation rates of cell groups treated with compound A or compound B were each calculated based on the cell group treated with DMSO as a control. The results were as shown in FIG. 6.

As shown in FIG. 6, both of compound A and B successfully and significantly reduce the viability of HTLV-1 infected cells (inducing HAM), which are derived from the cerebrospinal fluid, compared to the group treated with DMSO. From this, it was demonstrated that compound A and B are effective for treating HAM.

Next, in a 6-well plate, HCT-4 ($4.5 \times 10^5$ cells) or HCT-5 ($3.75 \times 10^5$ cells) were seeded. A solution of compound A or B prepared with DMSO was serially diluted (4-fold dilution from 10000 nM was serially repeated 8 times) and added thereto. The cells were repeatedly subcultured at intervals of 3 to 4 days in a culture solution of 3 mL in total at 37° C. in 5% $CO_2$ condition for 14 days. In the subculture, a culture solution containing HCT-4 in the DMSO-treated group were added to a new culture medium such that the cell number was $4.5 \times 10^5$ cells, whereas a culture solution containing HCT-5 in the DMSO-treated group such that the cell number was $3.75 \times 10^5$ cells, and then, further compound A or B was added so as to obtain the same concentration as above to prepare a culture solution of 3 mL in total. The cells cultured for 14 days in individual conditions were recovered and the density of the cells were measured. In this manner, the effect of compound A or B on cell proliferation was examined. The density of cells was determined by seeding the cultured cells (100 μL) per well in a 96-well plate, adding 10 μL of CCK-8 per well, incubating the cells at 37° C. for 3 hours and measuring absorbance at 450 nm by a plate reader. The proliferation rate of a group treated with compound A or compound B was calculated based on the group treated with DMSO as a control. The results were as shown in FIG. 7.

As shown in FIG. 7, compound A and B successfully reduced the viability of HTLV-1 infected cells established from the cerebrospinal fluid of a HAM patient in a concentration-dependent manner. $GI_{50}$ of compound A for HCT-4 cells was 7.63 nM and $GI_{50}$ of compound B for HCT-4 cells was 5.92 nM; whereas, $GI_{50}$ of compound A for HCT-5 cells was 185.4 nM and $GI_{50}$ of compound B for HCT-5 cells was 90.6 nM.

Example 6: Activity of EZH1/2 Dual Inhibitor to Induce Apoptosis of HAM Infection Cells In this Example, experiments were carried out using the cells cultured for 21 days in Example 5. To detect apoptotic cells in the cells cultured for 21 days by adding 1 μM of compound A or compound B, the cells were stained by use of PE Annexin V apoptosis Detection Kit I (BD) and analyzed by FACS. In this analysis, the viable cells were detected based on FSC (forward scatter)-SSC (side scatter) plots. The viable cells were analyzed by Annexin V-PE (annexin V) and 7-AAD (7-amino actinomycin D). Early apoptotic cells were detected as Annexin V (+) 7-AAD (−) cells. The results were as shown in FIG. 8 (HCT-4 cells) and FIG. 9 (HCT-5 cells).

Figure 8:
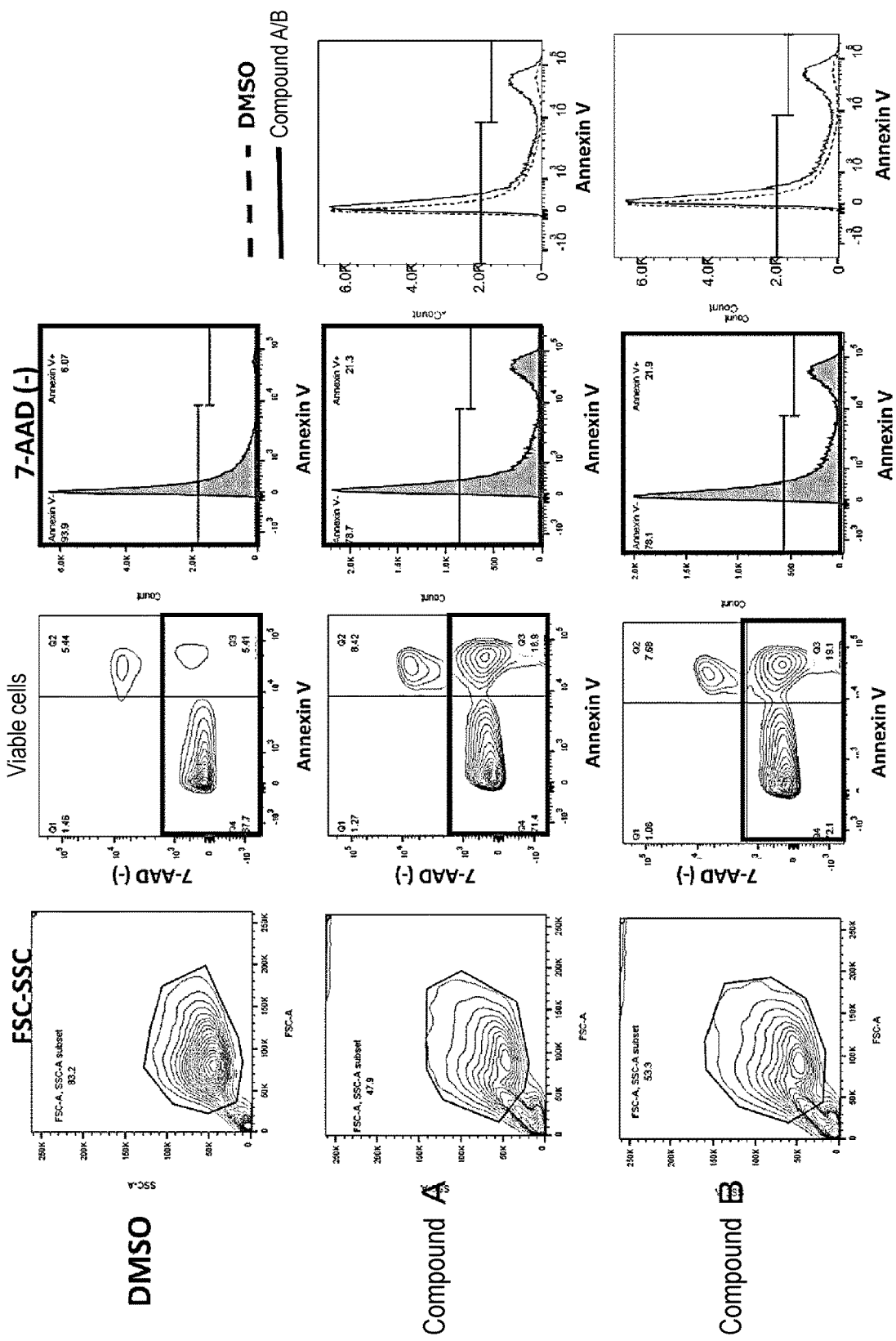
FIG. 8 shows that EZH1/2 dual inhibitors, compound A and compound B, each induce apoptosis of HTLV-1 infected cells established from the cerebrospinal fluid of a HAM patient.

As shown in FIG. 8, it was apparent that the number of viable cells decreases in HCT-4 cells treated with compound A or B. Also in FIG. 8, it was apparent that the number of early apoptotic cells increased in HCT-4 cells treated with compound A or B.

Figure 9:
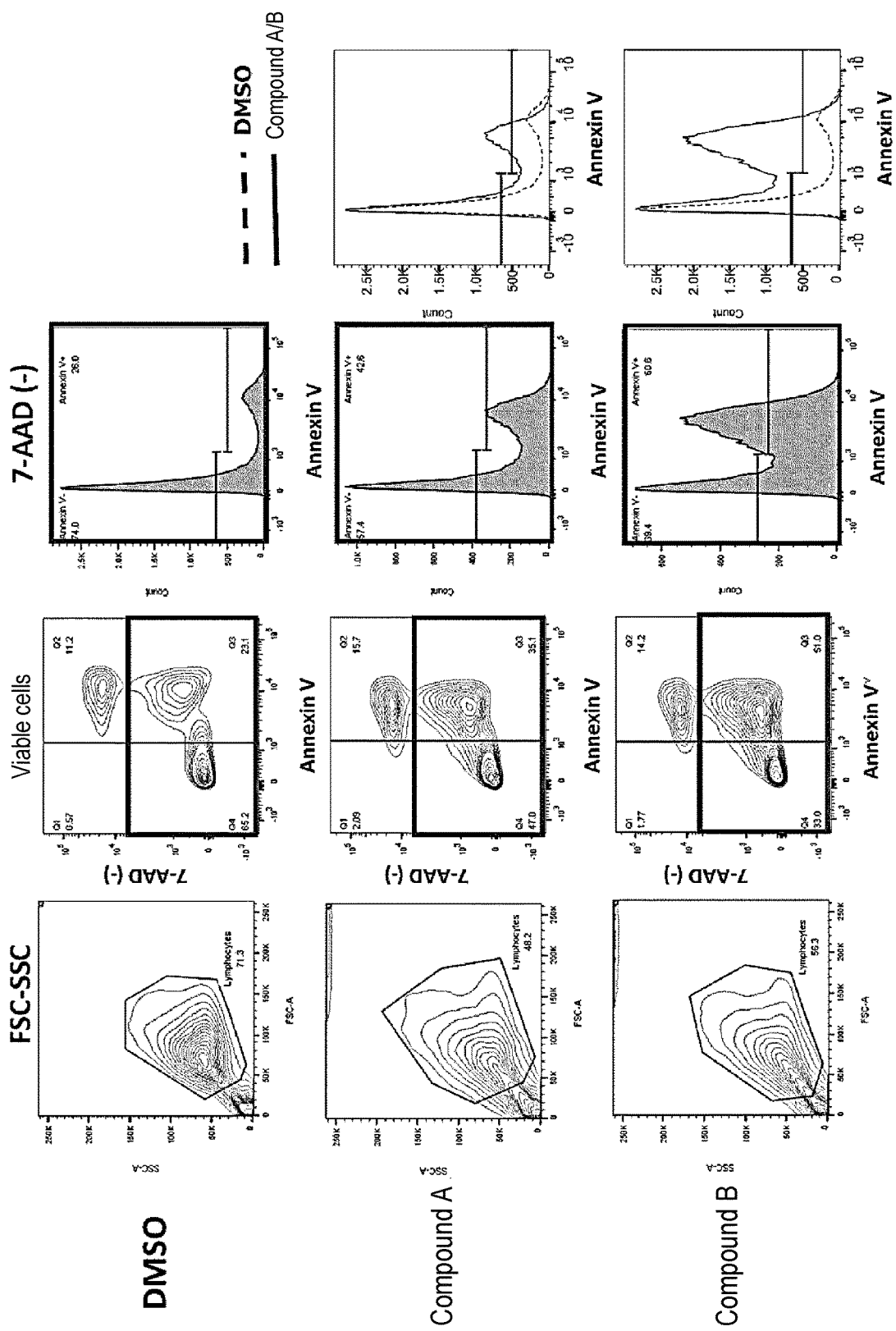
FIG. 9 shows that EZH1/2 dual inhibitors, compound A and compound B, each induce apoptosis of HTLV-1 infected cells established from the cerebrospinal fluid of a HAM patient, which differs from the patient of FIG. 8.

As shown in FIG. 9, it was apparent that the number of viable cells decreases in HCT-5 cells treated with compound A or B. Also in FIG. 9, it was apparent that the number of early apoptotic cells increased in HCT-5 cells treated with compound A or B.

The invention claimed is:

1. A method for treating HTLV-1-associated myelopathy in a subject in need thereof, comprising administering a therapeutically effective amount of an inhibitor selected from the group consisting of an EZH1 inhibitor, an EZH2 inhibitor and an EZH1/2 dual inhibitor to the patient.

2. The method according to claim 1, wherein the inhibitor is an EZH1/2 dual inhibitor.

3. The method according to claim 1, wherein the inhibitor is a compound selected from N-[(1,2-dihydro-4,6-dimethyl-2-oxo-3-pyridinyl)methyl]-3-methyl-1-[(1S)-1-methylpropyl]-6-[6(1-piperazinyl)-3-pyridinyl]-1H-indole-4-carboxamide, N-((4,6-dimethyl-2-oxo-1,2-dihydropyridin-3-yl)methyl)-5-(ethyl(tetrahydro-2H-piran-4-yl)amino)-4-methyl-4'-(morpholinomethyl)1,1'-biphenyl]-3-carboxamide, (2R)-7-bromo-2-[trans-4-(dimethylamino)cyclohexyl-N-[(4,6-dimethyl-2-oxo-1,2-dihydropyridin-3-yl)methyl]-2,4-dimethyl-1,3-benzodioxole-5-carboxamide, and (2R)-7-chloro-2-[trans-4-(dimethylamino)cyclohexyl-N-[(4,6-dimethyl-2-oxo-1,2-dihydropyridin-3-yl)methyl]-2,4-dimethyl-1,3-benzodioxole-5-carboxamide, or a pharmaceutically acceptable salt thereof.

4. The method according to claim 1, wherein the inhibitor is (2R)-7-bromo-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide, or (2R)-7-chloro-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide, or a pharmaceutically acceptable salt thereof.

5. The method according to claim 1, wherein the inhibitor is (2R)-7-bromo-2-[trans-4-(dimethylamino)cyclohexyl-N-[(4,6-dimethyl-2-oxo-1,2-dihydropyridin-3-yl)methyl]-2,4-dimethyl-1,3-benzodioxole-5-carboxamide, or a pharmaceutically acceptable salt thereof.

6. The method according to claim 1, wherein the inhibitor is (2R)-7-chloro-2-[trans-4-(dimethylamino)cyclohexyl-N-[(4,6-dimethyl-2-oxo-1,2-dihydropyridin-3-yl)methyl]-2,4-dimethyl-1,3-benzodioxole-5-carboxamide, or a pharmaceutically acceptable salt thereof.

7. The method according to claim 1, wherein the inhibitor is (2R)-7-chloro-2-[trans-4-(dimethylamino)cyclohexyl-N-[(4,6-dimethyl-2-oxo-1,2-dihydropyridin-3-yl)methyl]-2,4-dimethyl-1,3-benzodioxole-5-carboxamide p-toluene sulfonate.

8. A method for treating HTLV-1-associated myelopathy in a subject in need thereof, comprising administering a therapeutically effective amount of a compound selected form N-[(1,2-dihydro-4,6-dimethyl-2-oxo-3-pyridinyl)methyl]-3-methyl-1-[(1S)-1-methylpropyl]-6-[6(1-piperazinyl)-3-pyridinyl]-1H-indole-4-carboxamide, N-((4,6-dimethyl-2-oxo-1,2-dihydropyridin-3-yl)methyl)-5-(ethyl(tetrahydro-2H-piran-4-yl)amino)-4-methyl-4'-(morpholinomethyl)1,1'-biphenyl]-3-carboxamide, (2R)-7-bromo-2-[trans-4-(dimethylamino)cyclohexyl-N-[(4,6-dimethyl-2-oxo-1,2-dihydropyridin-3-yl)methyl]-2,4-dimethyl-1,3-benzodioxole-5-carboxamide, and (2R)-7-chloro-2-[trans-4-(dimethylamino)cyclohexyl-N-[(4,6-dimethyl-2-oxo-1,2-dihydropyridin-3-yl)methyl]-2,4-dimethyl-1,3-benzodioxole-5-carboxamide, or a pharmaceutically acceptable salt thereof to the subject.

9. The method according to claim 8, wherein a therapeutically effective amount of (2R)-7-bromo-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide, or a pharmaceutically acceptable salt thereof is administered to the subject.

10. The method according to claim 8, wherein a therapeutically effective amount of (2R)-7-chloro-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide, or a pharmaceutically acceptable salt thereof is administered to the subject.

11. The method according to claim 8, wherein a therapeutically effective amount of (2R)-7-chloro-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide p-toluene sulfonate is administered to the subject.

* * * * *